United States Patent [19]

Himmelsbach et al.

[11] Patent Number: 5,576,444

[45] Date of Patent: Nov. 19, 1996

[54] CYCLIC IMINO DERIVATIVES, PROCESSES FOR PREPARING THEM AND PHARMACEUTICAL COMPOSITIONS CONTAINING THESE COMPOUNDS

[75] Inventors: Frank Himmelsbach, Mittelbiberch; Austel Volkhard; Helmut Pieper, both of Biberach; Guenter Linz, Mittelbiberach; Johannes Weisenberger; Thomas Mueller, both of Biberach, all of Germany

[73] Assignee: Dr. Karl Thomae GmbH, Biberach an der Riss, Germany

[21] Appl. No.: 53,037

[22] Filed: Apr. 26, 1993

[30] Foreign Application Priority Data

Apr. 28, 1992 [DE] Germany ............................ 4213919.8

[51] Int. Cl.⁶ .................................................. C07D 207/26
[52] U.S. Cl. ........................... 548/413; 548/543; 548/551
[58] Field of Search ...................... 548/413, 543, 548/551; 514/91, 424

[56] References Cited

U.S. PATENT DOCUMENTS 4,491,591  1/1985  Abrahams ................................ 424/274

FOREIGN PATENT DOCUMENTS

| | | |
|---|---|---|
| 0196184 | 1/1986 | European Pat. Off. . |
| 0194548 | 9/1986 | European Pat. Off. . |
| 0350437 | 1/1990 | European Pat. Off. . |
| 0397044 | 11/1990 | European Pat. Off. . |
| 0409163 | 1/1991 | European Pat. Off. . |
| 0483667 | 5/1992 | European Pat. Off. . |
| 0503548 | 9/1992 | European Pat. Off. . |
| 0525629 | 2/1993 | European Pat. Off. . |
| 0528369 | 2/1993 | European Pat. Off. . |
| 2247166 | 2/1990 | Japan . |

*Primary Examiner*—Richard L. Raymond
*Assistant Examiner*—Brian G. Bembenick
*Attorney, Agent, or Firm*—Robert P. Raymond; Alan R. Stempel; Wendy E. Rieder

[57] ABSTRACT

Cyclic imino derivatives of the formula $$B-X_2-X_1-A-Y-E \qquad (I)$$

wherein A, B, E, $X_1$, $X_2$ and Y are as defined herein, the stereoisomers, tautomers, mixtures and addition salts thereof, pharmaceutical compositions containing these compounds and processes for preparing them. The cyclic imino derivatives are useful as inhibitors of cell-cell and cell-matrix interactions, e.g., thrombocyte aggregation.

5 Claims, No Drawings

CYCLIC IMINO DERIVATIVES, PROCESSES FOR PREPARING THEM AND PHARMACEUTICAL COMPOSITIONS CONTAINING THESE COMPOUNDS

The invention relates to cyclic imino derivatives of general formula $$B-X_2-X_1-A-Y-E \qquad (I)$$

the stereoisomers, the tautomers, the mixtures thereof and the salts thereof, particularly the physiologically acceptable salts thereof with inorganic or organic acids or bases which have, inter alia, valuable pharmacological properties, preferably aggregation-inhibiting effects, pharmaceutical compositions which contain these compounds, the use thereof and processes for preparing them.

In general formula I above, with the proviso that (i) B denotes an $R_1-CO-O-(R_2CR_3)-OCO-NH-C(=NH)-$ or $(R_4O)PO(OR_5)-NH-C(=NH)-$ group or E denotes a 1,3-dihydro-3-oxo-1-isobenzofuranyloxycarbonyl, $R_6-CO-O-CHR_7-O-CO-$ or $R_8O-CO-$ group or ii) B denotes an $R_1-CO-O-(R_2CR_3)-O-CO-NH-C(=NH)-$ or $(R_4O)PO(OR_5)-NH-C(=NH)-$ group and E denotes a 1,3-dihydro-3-oxo-1-isobenzofuranyloxycarbonyl, $R_6-CO-O-CHR_7-O-CO-$ or $R_8O-CO-$ group in which one of the two imino groups contained in the group B may additionally be substituted by a methyl group and $R_1$ denotes a $C_{1-15}$-alkyl group, a $C_{3-7}$-cycloalkyl group, a phenyl group or a phenylalkyl group having 1 to 3 carbon atoms in the alkyl moiety, $R_2$ and $R_3$, which may be identical or different, denote hydrogen atoms or $C_{1-6}$-alkyl groups or one of the groups $R_2$ or $R_3$ may additionally denote a $C_{3-7}$-cycloalkyl group or a phenyl group, $R_4$ and $R_5$, which may be identical or different, denote hydrogen atoms, $C_{1-4}$-alkyl groups, benzyl or phenyl groups, $R_6$ denotes a $C_{1-7}$-alkyl group, a $C_{2-7}$-alkenyl group, a $C_{3-7}$-cycloalkyl group, a $C_{1-6}$-alkoxy group, a $C_{4-7}$-cycloalkoxy group, a phenyl or phenoxy group, a phenylalkyl or phenylalkoxy group each having 1 to 3 carbon atoms in the alkyl moiety, or a 2-phenylvinyl or 3-phenylallyloxy group, $R_7$ denotes a hydrogen atom, a $C_{1-6}$-alkyl group, a $C_{3-7}$-cycloalkyl group or a phenyl group and $R_8$ denotes a $C_{4-8}$-cycloalkyl group or a cycloalkylalkyl group having 3 to 8 carbon atoms in the cycloalkyl moiety and 1 to 3 carbon atoms in the alkyl moiety, wherein the above-mentioned cycloalkyl moieties may additionally be substituted by 1 to 4 alkyl groups, by one or two alkoxy groups or by one or two dialkylamino groups which substituents may be identical or different and wherein the alkyl and alkoxy moieties may each contain 1 to 4 carbon atoms, or by a fluorine, chlorine or bromine atom, by a phenyl, trifluoromethyl or $C_{3-6}$-cycloalkyl group, and moreover, in the above-mentioned cycloalkyl moieties which contain 4 to 8 carbon atoms, a methylene group may be replaced by an oxygen or sulphur atom, by a $C_{1-4}$-alkylimino group or by a sulphinyl, sulphonyl, acetylimino or methanesulphonylimino group, a cycloalkenyl or cycloalkenylalkyl group each having 5 to 8 carbon atoms in the cycloalkenyl moiety and 1 to 3 carbon atoms in the alkyl moiety, wherein the above-mentioned cycloalkenyl moieties may additionally be substituted by 1 to 4 $C_{1-4}$-alkyl groups, with the proviso that the above-mentioned cycloalkenyl moieties are not linked to the oxygen atom of the adjacent O—CO group via a carbon atom from which a double bond starts, a bicycloalkyl or bicycloalkylalkyl group each having 6 to 10 carbon atoms in the bicycloalkyl moiety and 1 to 3 carbon atoms in the alkyl moiety, wherein the above-mentioned bicycloalkyl moieties may additionally be substituted by 1 to 3 methyl groups, a tricycloalkyl or tricycloalkylalkyl group each having 7 to 10 carbon atoms in the tricycloalkyl moiety and 1 to 3 carbon atoms in the alkyl moiety, wherein the above-mentioned tricycloalkyl moieties may additionally be substituted by 1 to 3 methyl groups, a bicycloalkenyl or bicycloalkenylalkyl group each having 7 to 10 carbon atoms in the bicycloalkenyl moiety and 1 to 3 carbon atoms in the alkyl moiety, wherein the above-mentioned bicycloalkenyl moieties may additionally be substituted by 1 to 3 methyl groups, with the proviso that the above-mentioned bicycloalkenyl moieties are not linked to the oxygen atom of the adjacent —O—CO— group via a carbon atom from which a double bond starts, a $C_{9-12}$-benzocycloalkyl group wherein the cycloalkyl moiety may be substituted by 1 or 2 methyl groups and the aromatic moiety may additionally be mono- or di-substituted by fluorine, chlorine or bromine atoms or by methyl, ethyl, methoxy, ethoxy, trifluoromethyl, cyano or methanesulphonyl groups and the substituents may be identical or different, an alkenyl or alkynyl group, each having 3 to 6 carbon atoms, optionally substituted by a phenyl group, with the proviso that the above-mentioned alkenyl or alkynyl groups are not linked to the oxygen atom of the adjacent —O—CO— group via a carbon atom from which a double or triple bond starts, wherein the above-mentioned phenyl groups may each be mono or disubstituted by fluorine, chlorine or bromine atoms or by methyl, ethyl, methoxy, ethoxy, trifluoromethyl, cyano or methanesulphonyl groups and the substituents may be identical or different, A denotes a pyrrolidine or 2-pyrrolidinone ring optionally substituted by the groups $R_9$ and $R_{10}$, wherein $R_9$ denotes a phenyl group which may be substituted by a fluorine, chlorine or bromine atom or by a methyl, methoxy, carboxy, methoxycarbonyl or dimethylaminocarbonyl group, a $C_{1-4}$-alkyl group optionally substituted by a cyclohexyl group or by two phenyl groups, or a straight-chained $C_{1-4}$-alkyl group substituted by a phenyl group which may be mono or disubstituted by $C_{1-4}$-alkyl, $C_{1-6}$-alkoxy, phenyl, benzyl, methylphenyl, methylsulphonyl or trifluoromethyl groups or by fluorine, chlorine or bromine atoms, wherein the substituents may be identical or different, a $C_{2-4}$-alkyl group substituted in the 2, 3 or 4-position by a hydroxy, methoxy or phenoxy group, a methyl group substituted by a carboxy, methoxycarbonyl, aminocarbonyl, methylaminobonyl, ethylaminocarbonyl, dimethylaminocarbonyl, diethylaminocarbonyl, benzylaminocarbonyl, pyrrolidinocarbonyl, piperidinocarbonyl or morpholinocarbonyl group, or, if A denotes a pyrrolidine ring, $R_9$ may denote a carbonyl group substituted by a methyl, phenyl, methylamino, ethylamino, dimethylamino, diethylamino or methoxymethyl group or $R_9$ may denote in 1-, 3- or 4-position a sulfonyl group substituted by a methyl, phenyl, methoxyphenyl or dimethylamino group or $R_9$ may denote in 1-position an aminomethylcarbonyl group, or, if A denotes a 2-pyrrolidinone ring, $R_9$ may denote in 3- or 4-position a sulfonyl group substituted by a methyl, phenyl, methoxyphenyl or dimethylamino group or $R_9$ may denote in 3-, 4- or 5-position a carbonyl group substituted by a methyl, phenyl, methylamino, ethylamino, dimethylamino, diethylamino or methoxymethyl group, and $R_{10}$ denotes a $C_{1-4}$-alkyl group, B denotes an $HNR_{11}$—C(=NH)— group wherein $R_{11}$ denotes a hydrogen atom, a $C_{1-4}$-alkyl group, an alkoxycarbonyl group having a total of 2 to 5 carbon atoms, a phenoxycarbonyl or benzyloxycarbonyl group, an $R_1$—CO—O—$(R_2CR_3)$—O—CO—NH—C(=NH)— or $(R_4O)PO(OR_5)$—NH—C(=NH)— group wherein $R_1$ to $R_5$ are defined as hereinbefore and one of the two imino groups contained in the group B may additionally be substituted by a methyl group, Y denotes a straight-chained or branched $C_{1-4}$-alkylene group, E denotes a carboxy, phosphono, O-methyl-phosphono or O-ethyl-phosphono group, a dialkylaminocarbonylmethoxycarbonyl group having 1 to 4 carbon atoms in the alkyl moiety, an alkoxycarbonyl group having a total of 2 to 7 carbon atoms, wherein the methoxy moiety may be substituted by a phenyl or pyridyl group, the ethoxy moiety by a phenyl or dimethoxyphenyl group or in the 2-position by a morpholino or 2-oxo-1-pyrrolidinyl group and the n-propoxy moiety may be substituted by a phenyl group, or E denotes a 1,3-dihydro-3-oxo-1-isobenzofuranyloxycarbonyl, $R_6$—CO—O—$CHR_7$—O—CO— or $R_8O$—CO— group, wherein $R_6$ to $R_8$ are defined as hereinbefore and the shortest distance of the group E from the first nitrogen atom of group B is at least 10 bonds, $X_1$ denotes a bond, a methylene group which, provided it is not bound to the ring nitrogen atom of group A, is bound to the adjacent $X_2$ group via an oxygen atom, a sulphonyl, —$NR_{12}$, —CO—NH—, —NH—CO— or —$SO_2$—NH— group, wherein $R_{12}$ denotes a hydrogen atom or a methyl, ethyl, acetyl or methanesulphonyl group and the sulphonyl group of the above-mentioned —$SO_2$—NH— group is linked to the group $X_2$, or $X_1$ denotes an ethylene group which is bound to the adjacent group $X_2$ via an oxygen atom or via a —CONH group, in which the carbonyl group of the CONH— group is linked to the group $X_2$, and $X_2$ denotes a biphenylylene group which may be substituted by a fluorine, chlorine, bromine or iodine atom, by a methyl, methoxy, ethoxy, trifluoromethyl, methylsulphenyl, methylsulphinyl, methylsulphonyl, nitro, acetylamino or methanesulphonylamino group or by another methyl group, or $X_1$ denotes a phenylenecycloalkylene group having a total of 10 to 12 carbon atoms, a phenylenesulphenylphenylene, phenylenesulphinylphenylene, phenylenesulphonylphenylene, dihydrophenanthrenylene, indanylene or naphthylene group or a fluorenylene group in which the methylene group may be replaced by a hydroxymethylene or carbonyl group.

Preferred compounds of general formula I above are those wherein, with the proviso that (i) B denotes an $R_1$—CO—O—$(R_2CR_3)$—O—CO—NH—C(=NH)— or $(R_4O)PO(OR_5)$—NH—C(=NH)— group or E denotes a 1,3-dihydro-3-oxo-1-isobenzofuranyloxycarbonyl, $R_6$—CO—O—$CHR_7$—O—CO— or $R_8O$—CO— group or (ii) B denotes an $R_1$—CO—O—$(R_2CR_3)$—O—CO—NH—C (=NH)— or $(R_4O)PO(OR_5)$—NH—C(=NH)— group and E denotes a 1,3-dihydro-3-oxo-1-isobenzofuranyloxycarbonyl, $R_6$—CO—O—$CHR_7$—O—CO— or $R_8O$—CO— group, wherein $R_1$ denotes a $C_{1-4}$-alkyl group or a phenylalkyl group having 1 to 3 carbon atoms in the alkyl moiety, $R_2$ denotes a hydrogen atom or a methyl or ethyl group, $R_3$ denotes a hydrogen atom, $R_4$ and $R_5$, which may be identical or different, denote hydrogen atoms or $C_{1-4}$-alkyl groups, $R_6$ denotes a $C_{1-7}$-alkyl, $C_{5-7}$-cycloalkyl, $C_{1-4}$-alkoxy, $C_{5-7}$-cycloalkoxy, phenyl or phenoxy group or a phenylalkyl or phenylalkoxy group each having 1 to 3 carbon atoms in the alkyl moiety, $R_7$ denotes a hydrogen atom, a $C_{1-3}$-alkyl group, a $C_{5-7}$-cycloalkyl group or a phenyl group and $R_8$ denotes a $C_{4-8}$-cycloalkyl group or a cycloalkylalkyl group having 3 to 8 carbon atoms in the cycloalkyl moiety and 1 to 3 carbon atoms in the alkyl moiety, whilst the above-mentioned cycloalkyl moieties may additionally be substituted by a $C_{1-4}$-alkyl group or by a $C_{1-4}$-alkyl group and 1 to 3 methyl groups or by an alkoxy or dialkylamino group each having 1 to 4 carbon atoms in the alkoxy or alkyl moiety and moreover a methylene group in the above-mentioned cycloalkyl moieties which contain 4 to 8 carbon atoms may be replaced by an oxygen or sulphur atom, by an alkylimino group having 1 to 4 carbon atoms in the alkyl moiety, or by a sulphinyl or sulphonyl group, with the proviso that there are at least two carbon atoms between the ring hetero atom and the next heteroatom, a cycloalkenyl or cycloalkenylalkyl group, each having 5 to 8 carbon atoms in the cycloalkenyl moiety and 1 to 3 carbon atoms in the alkyl moiety, whilst the above-mentioned cycloalkenyl moieties may additionally be substituted by a $C_{1-4}$-alkyl group or by a $C_{1-4}$-alkyl group and 1 to 3 methyl groups, with the proviso that the above-mentioned cycloalkenyl moieties are not linked to the oxygen atom of the adjacent —O—CO— group via a carbon atom from which a double bond starts, a bicycloalkyl or bicycloalkylalkyl group, each having 6 to 10 carbon atoms in the bicycloalkyl moiety and 1 to 3 carbon atoms in the alkyl moiety, wherein the above-mentioned bicycloalkyl moieties may additionally be substituted by 1 to 3 methyl groups, a bicycloalkenyl or bicycloalkenylalkyl group each having 7 to 10 carbon atoms in the bicycloalkenyl moiety and 1 to 3 carbon atoms in the alkyl moiety, wherein the above-mentioned bicycloalkenyl moieties may additionally be substituted by 1 to 3 methyl groups, with the proviso that the above-mentioned bicycloalkenyl moieties are not linked to the oxygen atom of the adjacent —O—CO— group via a carbon atom from which a double bond starts, a $C_{9-12}$-benzocycloalkyl group wherein the cycloalkyl moiety may be substituted by 1 or 2 methyl groups and the aromatic moiety may additionally be mono or disubstituted by fluorine, chlorine or bromine atoms or by methyl, ethyl, methoxy, ethoxy, trifluoromethyl, cyano or methanesulphonyl groups and the substituents may be identical or different, an alkenyl or alkynyl group, each having 3 to 6 carbon atoms, optionally substituted by a phenyl group, with the proviso that the above-mentioned alkenyl or alkynyl groups are not linked to the oxygen atom of the adjacent —O—CO— group via a carbon atom from which a double or triple bond starts, A denotes a pyrrolidine or 2-pyrrolidinone ring optionally substituted by the groups $R_9$ and $R_{10}$, wherein $R_9$ denotes a phenyl group, an optionally cyclohexyl-substituted $C_{1-4}$-alkyl group or a straight,chained $C_{1-4}$-alkyl group terminally substituted by a phenyl group which may be mono or disubstituted by $C_{1-2}$-alkyl, $C_{1-2}$-alkoxy, methylsulphonyl or trifluoromethyl groups or by fluorine or chlorine atoms, wherein the substituents may be identical or different, a $C_{2-4}$-alkyl group terminally substituted by a hydroxy, methoxy or phenoxy group, a methyl group substituted by a dimethylaminocarbonyl, pyrrolidinocarbonyl or morpholinocarbonyl group, or, if A denotes a pyrrolidine ring, $R_9$ may denote a carbonyl group substituted by a methyl, phenyl, dimethylamino or methoxymethyl group or $R_9$ may denote in 1-, 3- or 4-position a sulfonyl group substituted by a methyl, phenyl, methoxyphenyl or dimethylamino group, or, if A denotes a 2-pyrrolidinone ring, $R_9$ may denote in 3- or 4-position a sulfonyl group substituted by a methyl, phenyl, methoxyphenyl or dimethylamino group or $R_9$ may denote in 3-, 4- or 5-position a carbonyl group substituted by a methyl, phenyl, dimethylamino or methoxymethyl group and $R_{10}$ denotes an alkyl group having 1 or 2 carbon atoms, B denotes an $HNR_{11}$—C(=NH)— group wherein $R_{11}$ is a hydrogen atom, a $C_{1-2}$-alkyl group, an alkoxycarbonyl group having a total of 2 or 3 carbon atoms or a benzyloxycarbonyl group, an $R_1$—CO—O—$(R_2CR_3)$—O—CO—NH—C(=NH)— or $(R_4O)PO(OR_5)$—NH—C(=NH)— group wherein $R_1$ to $R_5$ are defined as mentioned hereinbefore, Y denotes a methylene group, E denotes a carboxy group, an alkoxycarbonyl group having a total of 2 to 7 carbon atoms in which the methoxy moiety may be substituted by a phenyl group, the ethoxy moiety by a phenyl or dimethoxyphenyl group and the n-propoxy moiety by a phenyl group, or E denotes a 1,3-dihydro-3-oxo-1-isobenzofuranyloxycarbonyl, $R_6$—CO—O—$CHR_7$—O—CO— or $R_8O$—CO— group, wherein $R_6$ to $R_8$ are defined as hereinbefore and the shortest distance of the group E from the first nitrogen atom of group B is at least 10 bonds, $X_1$ denotes a bond, a methylene group which, if it is not bound to the ring nitrogen atom of group A, is bound to the adjacent $X_2$ group via an oxygen atom or a sulphonyl, —$NR_{12}$—, —CO—NH— or —$SO_2NH$— group, wherein $R_{12}$ denotes a hydrogen atom or a methyl or acetyl group, or $X_1$ denotes an ethylene group which is bound to the adjacent $X_2$ group via a —CO—NH— group, whilst the carbonyl and sulphonyl group of the above-mentioned —CO—NH— and —$SO_2$—NH— groups are linked to the group $X_2$, and $X_2$ denotes a biphenylylene group which may be substituted by a fluorine or chlorine atom or by a methyl, methoxy, ethoxy, trifluoromethyl, methylsulphonyl, acetylamino or methanesulphonylamino group or by another methyl group, or $X_2$ denotes a phenylenecycloalkylene group having a total of 10 to 12 carbon atoms, a dihydrophenanthrenylene group or a fluorenylene group in which the methylene group may be replaced by a carbonyl group, particularly those compounds of general formula I wherein, with the proviso that (i) B denotes an $R_1$—CO—O—$(R_2CR_3)$—O—CO—NH—C(=NH)— or $(R_4O)PO(OR_5)$—NH—C(=NH)— group or E denotes a 1,3-dihydro-3-oxo-1-isobenzofuranyloxycarbonyl, $R_6$—CO—O—$CHR_7$—O—CO— or $R_8O$—CO— group or (ii) B denotes an $R_1$—CO—O—$(R_2CR_3)$—O—CO—NH—C(=NH)— or $(R_4O)PO(OR_5)$ —NH—C(=NH)— group and E denotes a 1,3-dihydro-3-oxo-1-isobenzofuranyloxycarbonyl, $R_6$—CO—O—$CHR_7$—O—CO— or $R_8O$—CO— group, wherein $R_1$ denotes a $C_{1-4}$-alkyl group, $R_2$ is a hydrogen atom or a methyl group, $R_3$ is a hydrogen atom, $R_4$ and $R_5$, which may be identical or different, denote hydrogen atoms or methyl or ethyl groups, $R_6$ denotes a $C_{1-4}$-alkyl group, a $C_{5-7}$-cycloalkyl group, a $C_{1-4}$-alkoxy group, a $C_{5-7}$-cycloalkoxy group or a phenyl group, $R_7$ denotes a hydrogen atom or a $C_{1-3}$-alkyl group and $R_8$ denotes a $C_{5-8}$-cycloalkyl group or a cycloalkylalkyl group having 3 to 8 carbon atoms in the cycloalkyl moiety and 1 to 3 carbon atoms in the alkyl moiety, whilst the above-mentioned cycloalkyl moieties may additionally be substituted by a $C_{1-4}$-alkyl group or by a $C_{1-4}$-alkyl group and 1 to 3 methyl groups, by an alkoxy or dialkylamino group each having 1 to 4 carbon atoms in the alkoxy and alkyl moieties and moreover in the cycloalkyl moieties mentioned above which contain 4 to 8 carbon atoms, a methylene group may be replaced by an oxygen atom or by a methylimino or ethylimino group, with the proviso that there are at least 2 carbon atoms between the ring heteroatom and the next heteroatom, a cycloalkenyl or cycloalkenylalkyl group each having 5 to 8 carbon atoms in the cycloalkenyl moiety and 1 to 3 carbon atoms in the alkyl moiety, whilst the above-mentioned cycloalkenyl moieties may additionally be substituted by one or two methyl groups, with the proviso that the above-mentioned cycloalkenyl moieties are not linked to the oxygen atom of the adjacent —O—CO— group via a carbon atom from which a double bond starts, a bicycloalkyl or bicycloalkylalkyl group each having 6 to 8 carbon atoms in the bicycloalkyl moiety and 1 to 3 carbon atoms in the alkyl moiety, in which the above-mentioned bicycloalkyl moieties may additionally be substituted by 1 to 3 methyl groups, a bicycloalkenyl or bicycloalkenylalkyl group each having 7 or 8 carbon atoms in the bicycloalkenyl moiety and 1 to 3 carbon atoms in the alkyl moiety, in which the above-mentioned bicycloalkenyl moieties may additionally be substituted by 1 to 3 methyl groups, with the proviso that the above-mentioned bicycloalkenyl moieties are not linked to the oxygen atom of the adjacent —O—CO— group via a carbon atom from which a double bond starts, a benzocycloalkyl group having a total of 9 to 11 carbon atoms, wherein the aromatic moiety may be substituted by a fluorine, chlorine or bromine atom, or by a methyl, ethyl, methoxy, ethoxy, tri fluoromethyl, cyano or methanesulphonyl group, an optionally phenyl-substituted alkenyl or alkynyl group each having 3 to 6 carbon atoms, with the proviso that the above-mentioned alkenyl or alkynyl groups are not linked to the oxygen atom of the adjacent —O—CO— group via a carbon atom from which a double or triple bond starts, A denotes a pyrrolidine or 2-pyrrolidinone ring optionally methyl-substituted in the carbon skeleton, wherein the pyrrolidine ring is substituted in the 1-position by an acetyl, benzoyl, dimethylaminocarbonyl, methoxyace-tyl, methanesulphonyl, phenylsulphonyl, 4-methoxyphenylsulphonyl or dimethylaminosulphonyl group and the pyrrolidinone ring is substituted in the 1-position by a phenyl group, by a straight-chained $C_{1-4}$-alkyl group terminally substituted by a phenyl group (which may be substituted by a methyl, methoxy, methanesulphonyl or trifluoromethyl group or by two methoxy groups), by a $C_{1-4}$-alkyl group which may be terminally substituted by a cyclohexyl group, by a straight-chained $C_{2-4}$-alkyl group terminally substituted by a methoxy or phenoxy group, or by a methyl group which is substituted by a dimethylaminocarbonyl, pyrrolidinocarbonyl or morpho-linocarbonyl group, B denotes an $HNR_{11}$—C(=NH)— group wherein $R_{11}$ denotes a hydrogen atom, an alkoxycarbonyl group having a total of 2 or 3 carbon atoms or a benzyloxycarbonyl group, an $R_1$—CO—O—$(R_2CR_3)$—O—CO—NH—C(=NH)— or $(R_4O)PO(OR_5)$—NH—C(=NH)— group wherein $R_1$ to $R_5$ are defined as hereinbefore, Y denotes a methylene group, E denotes a carboxy group, an alkoxycarbonyl group having a total of 2 to 7 carbon atoms in which the methoxy moiety may be substituted by a phenyl group, or E denotes a 1,3-dihydro-3-oxo-1-isobenzofuranyloxycarbonyl, $R_6$—CO—O—$CHR_7$—O—CO— or $R_8O$—CO— group, wherein $R_6$ to $R_8$ are defined as hereinbefore and the shortest distance of the group E from the first nitrogen atom of group B is at least 10 bonds, $X_1$ denotes a bond, a methylene group which, provided that it is not bound to the ring nitrogen atom of group A, is bound to the adjacent $X_2$ group via an oxygen atom or a sulphonyl, —$NR_{12}$—, —CO—NH— or —$SO_2$—NH— group, wherein $R_{12}$ denotes a hydrogen atom or a methyl or acetyl group and the carbonyl and sulphonyl group of the above-mentioned —CO—NH— and —$SO_2$—NH— groups is linked to the group $X_2$, and $X_2$ denotes a biphenylylene group which may be substituted by a fluorine or chlorine atom or by a methyl, methoxy, trifluoromethyl or methylsulphonyl group or by another methyl group, or $X_2$ denotes a phenylenecyclohexylene or 9,10-dihydrophenanthrenylene group or a fluorenylene group in which the methylene group may be replaced by a carbonyl group, the stereoisomers thereof, the tautomers thereof, the mixtures and salts thereof.

Particularly preferred compounds of general formula I above are those wherein, with the proviso that (i) B denotes an $R_1$—CO—O—$(R_2CR_3)$—O—CO—NH—C(=NH)— or $(R_4O)PO(OR_5)$—NH—C(=NH)— group or E denotes an $R_6$—CO—O—$CHR_7$—O—CO— or $R_8O$—CO— group or (ii) B denotes an $R_1$—CO—O—$(R_2CR_3)$—O—CO—NH—C(=NH)— or $(R_4O)PO(OR_5)$—NH—C(=NH)— group and E denotes an $R_6$—CO—O—$CHR_7$—O—CO— or $R_8O$—CO— group, wherein $R_1$ denotes a $C_{1-4}$-alkyl group, $R_2$ denotes a hydrogen atom or a methyl group, $R_3$ denotes a hydrogen atom, $R_4$ and $R_5$, which may be identical or different, represent methyl or ethyl groups, $R_6$ denotes a $C_{1-4}$-alkyl group, a cyclohexyl or phenyl group, a $C_{1-4}$-alkoxy group or a $C_{5-7}$-cycloalkoxy group, $R_7$ denotes a hydrogen atom or a methyl group and $R_8$ denotes a cycloalkyl, cycloalkylmethyl or cycloalkylethyl group each having 5 to 8 carbon atoms in the cycloalkyl moiety, in which the above-mentioned cycloalkyl moieties may additionally be substituted by a $C_{1-4}$-alkyl group or by a $C_{1-4}$-alkyl group and 1 to 3 methyl groups, by a methoxy, ethoxy, dimethylamino or diethylamino group and moreover, in the above-mentioned cycloalkyl moieties, a methylene group may be replaced by an oxygen atom or by a methylimino or ethylimino group, with the proviso that there are at least two carbon atoms between the ring heteroatom and the next heteroatom, a cyclohexenyl or cyclohexenylmethyl group, in which the above-mentioned cyclohexenyl moieties may additionally be substituted by a methyl group, with the proviso that the above-mentioned cyclohexenyl moieties are not linked to the oxygen atom of the adjacent —O—CO— group via a carbon atom from which a double bond starts, a bicycloalkyl or bicycloalkylalkyl group each having 6 to 8 carbon atoms in the bicycloalkyl moiety and 1 or 2 carbon atoms in the alkyl moiety, whilst the above-mentioned bicycloalkyl moieties may additionally be substituted by 1 to 3 methyl groups, a bicycloalkenyl or bicycloalkenylalkyl group each having 7 or 8 carbon atoms in the bicycloalkenyl moiety and 1 or 2 carbon atoms in the alkyl moiety, whilst the above-mentioned bicycloalkenyl moieties may additionally be substituted by 1 to 3 methyl groups, with the proviso that the above-mentioned bicycloalkenyl moieties are not linked to the oxygen atom of the adjacent —O—CO— group via a carbon atom from which a double bond starts, a benzocycloalkyl group having a total of 9 or 10 carbon atoms, an alkenyl or alkynyl group each having 3 to 5 carbon atoms, with the proviso that the above-mentioned alkenyl or alkynyl groups are not linked to the oxygen atom of the adjacent —O—CO— group via a carbon atom from which a double or triple bond starts, or a cinnamyl group, A denotes a 2-pyrrolidinone ring optionally methyl-substituted in the carbon skeleton, B denotes an $HNR_{11}$—C(=NH)— group wherein $R_{11}$ represents a hydrogen atom, a methoxycarbonyl, ethoxycarbonyl or benzyloxycarbonyl group, an $R_1$—CO—O—($R_2CR_3$)—O—CO—NH—C(=NH)— or $(R_4O)PO(OR_5)$—NH—C(=NH)— group, wherein $R_1$ to $R_5$ are defined as hereinbefore, Y denotes a methylene group, E denotes a carboxy group, an alkoxycarbonyl group having
a total of 2 to 6 carbon atoms, an $R_6$—CO—O—$CHR_7$—O—CO— or $R_8O$—CO— group, wherein $R_6$ to $R_8$ are defined as hereinbefore and the shortest distance of group E from the first nitrogen atom of group B is at least 10 bonds, $X_1$ denotes a methylene group which, provided it is not bound to the ring nitrogen atom of group A, is bound to the adjacent $X_2$ group via an oxygen atom or a sulphonyl, —CO—NH— or —$SO_2$—NH— group, in which the carbonyl and sulphonyl groups of the above-mentioned —CO—NH— and —$SO_2$—NH— groups are linked to the group $X_2$, and $X_2$ denotes a biphenylylene group which may be substituted by a fluorine or chlorine atom, by a methyl or trifluoromethyl group or by another methyl group, the stereoisomers thereof, the tautomers thereof, the mixtures and salts thereof.

Most particularly preferred compounds of general formula I above are those wherein, with the proviso that (i) B denotes an Ri—CO—O—($R_2CR_3$)—O—CO—NH—C(=NH)— or $(R_4O)PO(OR_5)$—NH—C(=NH)— group or E denotes an $R_6$—CO—O—$CHR_7$—O—CO— or $R_8O$—CO— group or (ii) B denotes an $R_1$—CO—O—($R_2CR_3$)—O—CO—NH—C(=NH)— or $(R_4O)PO(OR_5)$ —NH—C(=NH)— group and E denotes an $R_6$—CO—O—$CHR_7$—O—CO— or $R_8O$—CO— group, wherein $R_1$ denotes a methyl group, $R_2$ denotes a hydrogen atom or a methyl group, $R_3$ denotes a hydrogen atom, $R_4$ and $R_5$ each denotes an ethyl group, $R_6$ denotes a tert.butyl group or an ethoxy or cyclohexyloxy group, $R_7$ denotes a hydrogen atom or a methyl group and $R_8$ denotes a cyclopentyl, cyclohexyl, cycloheptyl or cyclohexylmethyl group, A denotes a 2-pyrrolidinone ring, B denotes an $HNR_{11}$—C(=NH)— group wherein $R_{11}$ represents a hydrogen atom, a methoxycarbonyl or benzyloxycarbonyl group, an $R_1$—CO—O—($R_2CR_3$)—O—CO—NH—C(=NH)— or $(R_4O)PO(OR_5)$—NH—C(=NH)— group wherein $R_1$ to $R_5$ are defined as hereinbefore, Y denotes a methylene group, E denotes a methoxycarbonyl group, an $R_6$—CO—O—$CHR_7O$—CO— or $R_8O$—CO— group, wherein $R_6$ to $R_8$ are as hereinbefore defined and the shortest spacing of group E from the first nitrogen atom of group B is at least 10 bonds, $X_1$ and $X_2$ together denote a 4-biphenylyleneoxymethylene group, wherein the group B in the 4'-position is linked to the 4-biphenylyleneoxymethylene group, and the methylene group of the 4-biphenylyleneoxymethylene group is linked to a carbon atom of group A, particularly those compounds wherein A, B, E, $X_1$, $X_2$ and Y are as hereinbefore defined, the group —Y—E is in position 3 and the group B-$X_2$—$X_1$— is in position 5 of the 2-pyrrolidinone ring, the stereoisomers, tautomers, mixtures and salts thereof.

The following are examples of particularly preferred compounds of general formula I above:

(3S,5S)-5-[(4'-acetoxymethyloxycarbonylamidino-4-biphenylyl)oxymethyl]-3-[(methoxycarbonyl)methyl]-2pyrrolidinone, (3S,5S)-5-[[4'-(1-acetoxyethyl)oxycarbonylamidino-4-biphenylyl]oxymethyl]-3-[(methoxycarbonyl)methyl]-2pyrrolidinone, (3S,5S)-5-[(4'-benzyloxycarbonylamidino-4-biphenylyl)oxymethyl]-3-[[[1-(cyclohexyloxycarbonyloxy-)ethyl]oxycarbonyl]methyl]-2-pyrrolidinone, (3S,5S)-5-[(4'-benzyloxycarbonylamidino-4-biphenylyl)oxymethyl]-3-[[[l(ethyloxycarbonyloxy)ethyl]oxycarbonyl]methyl]-2-pyrrolidinone, (3S,5S)-5-[(4'-benzyloxycarbonylamidino-4-biphenylyl)oxymethyl]-3-[(pivaloyloxymethyloxycarbonyl)methyl]-2-pyrrolidinone, (3S,5S)-5-[(4'-methoxycarbonylamidino-4-biphenylyl)oxymethyl]-3-[(pivaloyloxymethyloxycarbonyl)methyl]-2-pyrrolidinone, (3S,5S)-5-[(4'-amidino-4-biphenylyl)oxymethyl]-3-[[[1-(cyclohexyloxycarbonyloxy)ethyl]oxycarbonyl]methyl]-2-pyrrolidinone, (3S,5S)-5-[(4'-amidino-4-biphenylyl)oxymethyl]-3-[[[1-(ethyloxycarbonyloxy) ethyl]oxycarbonyl]methyl]-2-pyrrolidinone, (3S,5S)-5-[(4'-amidino-4-biphenylyl)oxymethyl]-3-[(pivaloyloxymethyloxycarbonyl)methyl]-2-pyrrolidinone, (3S,5S)-5-[(4'-amidino-4-biphenylyl) oxymethyl]-3-[(cyclohexyloxycarbonyl)methyl]-2-pyrrolidinone, (3S,5S)-5-[(4'-amidino-4-biphenylyl) oxymethyl]-3-[(cyclohexylmethyloxycarbonyl)methyl]-2-pyrrolidinone, (3S,5S)-5-[(4'-amidino-4-biphenylyl)oxymethyl]-3-[(cyclopentyloxycarbonyl)methyl]-2-pyrrolidinone, (3S,5S)-5-[(4'-amidino-4-biphenylyl)oxymethyl]-3-[(cycloheptyloxycarbonyl)methyl]-2-pyrrolidinone, (3S,5S)-3-[(cyclohexyloxycarbonyl)methyl]-5-[(4'-methoxycarbonylamidino-4-biphenylyl)oxymethyl]-2-pyrrolidinone, (3S,5S)-5-[[4 '-(O,O'diethylphosphono)amidino-4-biphenylyl]oxymethyl]-3-[(methoxycarbonyl)methyl]-2-pyrrolidinone and the salts thereof.

According to the invention, the new compounds of general formula I are obtained by the following methods:

a) In order to prepare compounds of general formula I wherein B denotes an $R_1$—CO—O—($R_2CR_3$)—O—CO—NH—C(=NH)— or $HNR_{11}$—C(=NH)— group, wherein $R_1$, $R_2$ and $R_3$ are as hereinbefore defined, $R_{11}$ denotes an alkoxycarbonyl group having a total of 2 to 5 carbon atoms or a phenoxycarbonyl or benzyloxycarbonyl group and additionally one of the two imino groups in the above-mentioned groups may be substituted by a methyl group:

Reacting a compound of general formula $H_2N$—C(=NH)—$X_2$—$X_1$—A—Y—E         (II)

wherein

A, $X_1$, $X_2$ and Y are as hereinbefore defined, whilst additionally an amino or imino group in the above-mentioned $H_2N-C(=NH)-$ group may be substituted by a methyl group, with a compound of general formula $$Z_1-B_1 \qquad\qquad (III)$$

wherein $B_1$ denotes an alkoxycarbonyl group having a total of 2 to 5 carbon atoms, a phenoxycarbonyl group, a benzyloxycarbonyl group or an $R_1-CO-O-(R_2CR_3)-O-CO-$ group in which $R_1$ to $R_3$ are defined as hereinbefore, and $Z_1$ denotes a nucleophilic leaving group such as a halogen atom or an aryloxy group, e.g. a chlorine or bromine atom or a p-nitrophenoxy group.

The reaction is conveniently carried out in a solvent such as tetrahydrofuran, methylene chloride, chloroform, ethyl acetate or dimethylformamide, expediently in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between 30° and 100° C., but preferably at temperatures between 10° and 60° C.

b) In order to prepare compounds of general formula I wherein E denotes a dialkylaminocarbonylmethoxycarbonyl group having 1 to 4 carbon atoms in the alkyl moiety, an alkoxycarbonyl group having a total of 2 to 7 carbon atoms, wherein the methoxy moiety may be substituted by a phenyl or pyridyl group, the ethoxy moiety may be substituted by a phenyl or dimethoxyphenyl group or in the 2-position by a morpholino or 2-oxo-1-pyrrolidinyl group and the n-propoxy moiety may be substituted by a phenyl group, or E denotes a 1,3-dihydro-3-oxo-1-isobenzofuranyloxycarbonyl, $R_6-CO-O-CHR_7-O-CO-$ or $R_8-O-CO-$ group:

Reacting a compound of general formula $$B-X_2-X_1-A-Y-COOH \qquad\qquad (IV)$$

wherein

A, B, $X_1$, $X_2$ and Y are as hereinbefore defined, with a compound of general formula $$Z_2-E_1 \qquad\qquad (V)$$

wherein $E_1$ denotes a dialkylaminocarbonylmethyl group having 1 to 4 carbon atoms in the alkyl moiety, an alkyl group having a total of 1 to 6 carbon atoms, wherein the methyl moiety may be substituted by a phenyl or pyridyl group, the ethyl moiety by a phenyl or dimethoxyphenyl group or in the 2-position by a morpholino or 2-oxo-1-pyrrolidinyl group and the n-propyl moiety may be substituted by a phenyl group, or $E_1$ denotes a 1,3-dihydro-3-oxo-1-isobenzofuranyl, $R_6-CO-O-CHR_7-$ or $R_8-$ group, wherein $R_6$ to $R_8$ are defined as hereinbefore, and $Z_2$ denotes a nucleophilic leaving group such as a halogen atom, e.g. a chlorine, bromine or iodine atom.

The reaction is conveniently carried out in a solvent such as methylene chloride, tetrahydrofuran, dioxane, dimethylsulphoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methyl-morpholine, which may simultaneously be used as solvent, or optionally in the presence of silver carbonate or silver oxide, at temperatures between 30° and 100° C., but preferably at temperatures between 10° and 80° C.

c) In order to prepare compounds of general formula I wherein E denotes a dialkylaminocarbonylmethoxycarbonyl group having 1 to 4 carbon atoms in the alkyl moiety, an alkoxycarbonyl group having a total of 2 to 7 carbon atoms, in which the methoxy moiety may be substituted by a phenyl or pyridyl group, the ethoxy moiety by a phenyl or dimethoxyphenyl group or in the 2-position by a morpholino or 2-oxo-1-pyrrolidinyl group and the n-propoxy moiety may be substituted by a phenyl group, or E denotes an $R_8O-CO-$ group:

Reacting a compound of general formula $$B-X_2-X_1-A-Y-COOH \qquad\qquad (IV)$$

wherein

A, B, $X_1$, $X_2$ and Y are as hereinbefore defined, with a compound of general formula $$HO-E_2 \qquad\qquad (VI)$$

wherein $E_2$ denotes a dialkylaminocarbonylmethyl group having 1 to 4 carbon atoms in the alkyl moiety, an alkyl group having a total of 1 to 6 carbon atoms, in which the methyl moiety may be substituted by a phenyl or pyridyl group, the ethyl moiety by a phenyl or dimethoxyphenyl group or in the 2-position by a morpholino or 2-oxo-1-pyrrolidinyl group and the n-propyl moiety may be substituted by a phenyl group, or an $R_8$ group, wherein $R_8$ is as hereinbefore defined.

The esterification is conveniently carried out in a suitable solvent or mixture of solvents, e.g. in a corresponding alcohol such as methanol, ethanol, isopropanol or cyclohexanol, methylene chloride, tetrahydrofuran, dioxane, pyridine, toluene or dimethylformamide in the presence of an acid-activating and/or dehydrating agent such as hydrogen chloride, conc. sulphuric acid, thionyl chloride, titanium tetrachloride, trimethylchlorosilane, ethylchloroformate, carbonyldiimidazole or N,N'-dicyclohexyl-carbodiimide or the isourea esters thereof, optionally in the presence of a reaction accelerator such as copper chloride, at temperatures between 0° and 100° C., but preferably at temperatures between 20° C. and 80° C.

d) In order to prepare compounds of general formula I wherein B denotes an $(R_4O)PO(OR_5)-NH-C(=NH)-$ group, wherein $R_4$ and $R_5$, which may be identical or different, denote $C_{1-4}$-alkyl groups, benzyl or phenyl groups and additionally one of the two imino groups in the above-mentioned group may be substituted by a methyl group:

Reacting a compound of general formula $$H_2N-C(=NH)-X_2-X_1-A-Y-E \qquad\qquad (II)$$

wherein

A, E, $X_1$, $X_2$ and Y are defined as hereinbefore, whilst additionally an amino or imino group in the above-mentioned $H_2N-C(=NH)-$ group may be substituted by a methyl group, with a compound of general formula $$(R_4'O)PO(OR_5')-Z_3 \qquad\qquad (VII)$$

wherein

R$_4$ and R$_5'$, which may be identical or different, denote C$_{1-4}$-alkyl groups, benzyl or phenyl groups and Z$_3$ denotes a nucleophilic leaving group such as a cyano group or a halogen atom, e.g. a chlorine or bromine atom.

The reaction is conveniently carried out in a solvent or mixture of solvents such as tetrahydrofuran, methylene chloride, chloroform, ethyl acetate or dimethylformamide, expediently in the presence of an inorganic base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between 30° C. and 100° C., but preferably at temperatures between 10° C. and 60° C. In the reactions described hereinbefore, any reactive groups present such as hydroxy, carboxy, phosphono, O-methyl-phosphono, O-ethyl-phosphono, amino, alkylamino, imino or amidino groups may be protected during the reaction by means of conventional protecting groups which are cleaved again after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, the protecting group for an amidino group may be the benzyloxycarbonyl group, the protecting group for a phosphono group may be a phenyl, methyl, ethyl or benzyl group, and the protecting group for an amino, alkylamino or imino group may be an acetyl, benzoyl, ethoxycarbonyl, tert.butoxycarbonyl, benzyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aproticly, e.g. in the presence of iodotrimethylsilane, at temperatures between −10° and 100° C., preferably at temperatures between 0° and 60° C.

However, a benzyl, methoxybenzyl or benzyloxycarbonyl group may be cleaved hydrogenolytically, for example, using hydrogen in the presence of a catalyst such as palladium/charcoal in a solvent such as methanol, ethanol, ethyl acetate or glacial acetic acid, optionally with the addition of an acid such as hydrochloric acid, at temperatures between 0° and 50° C., but preferably at ambient temperature, under a hydrogen pressure of 1 to 7 bar, preferably 3 to 5 bar.

A methoxybenzyl group may also be cleaved in the presence of an oxidising agent such as cerium(IV)-ammonium nitrate, in a solvent such as methylene chloride, acetonitrile or acetonitrile/water, at temperatures between 0° and 50° C., but preferably at ambient temperature.

However, a 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxane or ether.

The cleaving of only one alkyl group from an O,O'-dialkylphosphono group is preferably carried out using sodium iodide in a solvent such as acetone, ethylmethylketone, acetonitrile or dimethylformamide, at temperatures between 40° and 150° C., but preferably at temperatures between 60° and 100° C.

The cleaving of both alkyl groups from an O,O'-dialkylphosphono group is carried out, for example, with iodotrimethylsilane, bromotrimethylsilane or chlorotrimethylsilane/sodium iodide, in a solvent such as methylene chloride, chloroform or acetonitrile, at temperatures between 0° C. and the boiling temperature of the reaction mixture, but preferably at temperatures between 20° and 60° C.

The cleaving of a phthalyl group is preferably carried out in the presence of hydrazine or a primary amine such as methylamine, ethylamine or n-butylamine, in a solvent such as methanol, ethanol, isopropanol, toluene/water or dioxane, at temperatures between 20° and 50° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I obtained, which occur in racemate form, may be separated by methods known per se (cf. Allinger N. L. and Eliel E. L. in "Topics in Stereochemistry", Vol. 6, Wiley Interscience, 1971) into their optical antipodes and compounds of general formula I having at least 2 asymmetric carbon atoms may be separated on the basis of their physical-chemical differences using known methods, e.g. by chromatography and/or fractional crystallisation, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with optically active substances, especially acids and the activated derivatives or alcohols thereof, which form salts or derivatives, such as for example esters or amides, with the racemic compound, and separation of the diastereomeric salt or derivative mixture thus obtained, e.g. on the basis of their different solubilities, whilst the free antipodes may be released from the pure diastereomeric salts or derivatives by the action of suitable agents. Particularly common, optically active acids include, for example, the D and L-forms of tartaric acid or dibenzoyltartaric acid, di-o-tolyl tartaric acid, malic acid, mandelic acid, camphorsulphonic acid, glutamic acid, aspartic acid or quinic acid. Examples of an optically active alcohol include (+) or ()-menthol and examples of an optically active acyl group in amides include (+) or ()-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, acetic acid, fumaric acid, succinic acid, lactic acid, citric acid, tartaric acid or maleic acid.

In addition, the new compounds of formula I thus obtained, if they contain an acid group such as a carboxyl or phosphono group, may subsequently, if desired, be converted into the salts thereof with inorganic or organic bases, more particularly, for pharmaceutical use, into the physiologically acceptable salts thereof. Examples of suitable bases include sodium hydroxide, potassium hydroxide, ammonia, cyclohexylamine, ethanolamine, diethanolamine and triethanolamine.

The compounds used as starting materials are known from the literature in some cases or may be obtained by methods known from the literature as described in Examples I to X.

For example, a compound of general formula II is obtained by reacting a corresponding nitrile with an alcohol such as methanol, ethanol or propanol in the presence of an acid such as hydrochloric acid or by reacting a corresponding amide with a trialkyloxonium salt such as triethyloxonium-tetrafluoroborate, conveniently in a solvent such as methylene chloride, tetrahydrofuran or dioxane, or by reacting a corresponding nitrile with hydrogen sulphide, conveniently in a solvent such as pyridine or dimethylformamide, and subsequent alkylation of the resulting thioamide with an alkyl halide and subsequent reaction of an iminoester or iminothioester thus obtained with ammonia, methylamine or with a corresponding acid addition salt such as ammonium carbonate or ammonium acetate.

For example, a compound of general formula IV is obtained by cleaving a corresponding ester in an aqueous solvent, e.g. in water, water/tetrahydrofuran or water/methanol, in the presence of an alkali metal base such as sodium hydroxide or potassium hydroxide or in the presence of an acid such as hydrochloric acid, sulphuric acid or trifluoroacetic acid. A compound of general formula IV wherein B denotes an amidino group substituted by an alkoxycarbonyl or benzyloxycarbonyl group is obtained for example by reacting a corresponding amidino compound with a corresponding alkoxycarbonyl or benzyloxycarbonyl halide before the above-mentioned ester cleaving.

As already mentioned, the new cyclic imino derivatives of general formula I and the salts thereof, particularly the physiologically acceptable salts thereof with inorganic or organic acids or bases, have valuable properties. Thus, the new compounds of general formula I have valuable pharmacological properties and in addition to having an inhibitory effect on inflammation and bone degradation, have, in particular, antithrombotic, antiaggregatory and tumour or metastasis-inhibiting effects.

By way of example, the compounds of general formula I were investigated for their biological effects as follows:

The inhibition of thrombocyte aggregation after oral administration of the test substance is determined ex vivo on Rhesus monkeys.

Immediately before the oral administration of the test substance suspended in Natrosol, a blood sample is taken from the cubital vein of the animals as a reference value. At specific times after the administration of the substance fresh blood samples are taken and examined as follows.

The whole blood mixed with 3.14% sodium citrate in a ratio by volume of 1:10 is centrifuged at 200 g for 15 minutes. The supernatant platelet-rich plasma is carefully removed. From the erythrocyte-rich sediment, the platelet-impoverished plasma is obtained as supernatant by centrifuging at 4000 g for 10 minutes.

The thrombocyte aggregation induced in these ex vivo samples by means of collagen (Hormonchemie, Munich; 2 µg/ml final concentration in the platelet rich plasma) is measured photometrically using the method of Born and Cross (J. Physiol. 170:397 (1964)). The maximum light transmittance of the platelet rich plasma measured after collagen stimulation is compared with the reference value in order to determine the inhibition of aggregation at the various times of blood sampling after the administration of the substance, in relation to the reference value.

The compounds of Examples 1 and 3 inhibit the collagen-induced thrombocyte aggregation ex vivo after the oral administration of 1 mg/kg for more than 8 and for more than 4 hours, respectively.

After oral administration of 3 mg/kg the compound of Example 4 inhibits the collagen-induced thrombocyte aggregation ex vivo for longer than 8 hours.

The compounds according to the invention are well tolerated since, for example, the approximate LD50 of the compounds of Examples 1 and 3 in the mouse is above 300 mg/kg and that of the compound of Example 4 is above 100 mg/kg, after oral administration in each case.

In the light of their inhibitory effect on cell-cell or cell-matrix interactions, the new cyclic imino derivatives of general formula I and the physiologically acceptable salts thereof are suitable for combating or preventing diseases in which smaller or larger cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 µg and 30 mg/kg of body weight, preferably 1 µg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, -receptor antagonists, alkylnitrates such as glycerol trinitrate, phospho-diesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudin, inhibitors of thrombin or other activated clotting factors, may be incorporated together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:
Starting compounds:

EXAMPLE I (S)-1-(Benzyloxycarbonyl)-5-[(trityloxy)methyl]-2-pyrrolidinone

A solution of 160 g of (S)-5-[(trityloxy)methyl]-2-pyrrolidinone in 1600 ml of dry tetrahydrofuran is mixed within 35 minutes at −65° C. with 179 ml of a 2.5M solution of butyllithium in hexane. After 10 minutes at −65° C., a solution of 66.8 ml of benzylchloroformate in 100 ml of dry tetrahydrofuran is added dropwise and the resulting mixture is stirred for one hour. Then 200 ml of saturated saline solution are added and the tetrahydrofuran is eliminated by rotary evaporation. The residue is distributed between 3.5 liters of ethyl acetate and 200 ml of water, the organic phase is separated off and washed twice each with water and saline solution. The organic phase is separated off, dried and concentrated by rotary evaporation. The crude product is recrystallised from a little ethanol.

Yield: 181 g (82% of theory),

Melting point: 103°–105° C.

$R_f$ value: 0.53 (silica gel; cyclohexane/ethyl acetate=2:1)

| Calculated: | C 78.19 | H 5.95 | N 2.85 |
|---|---|---|---|
| Found: | 78.34 | 6.00 | 3.10 |

EXAMPLE II (3S,5S)-1-(Benzyloxycarbonyl)-3-[(tert.butyloxycarbonyl)methyl]-5-[(trityloxy)methyl]-2-pyrrolidinone To 20.0 g of (S)-1-(benzyloxycarbonyl)-5-[(trityloxy)methyl]-2-pyrrolidinone in 200 ml of dry tetrahydrofuran, 40.6 ml of a 1 molar solution of lithium hexamethyldisilazide in tetrahydrofuran are added dropwise at −65° C. After 10 minutes a solution of 6.57 ml of tert.butylbromoacetate in 20 ml of dry tetrahydrofuran is added dropwise. After 2 hours stirring at −65° C. the mixture is heated to 0° C. and 20 ml of a saturated aqueous ammonium chloride solution are added. The mixture is evaporated down in vacuo, the residue is mixed with 500 ml of ethyl acetate and extracted twice with water and once with saturated saline solution. The organic phase is dried, concentrated by rotary evaporation and the residue is purified by chromatography over a silica gel column with cyclohexane/ethyl acetate=4:1.

Yield: 20.0 g (81% of theory), $R_f$ value: 0.66 (silica gel; cyclohexane/ethyl acetate=2:1)

| Calculated: | C 75.35 | H 6.49 | N 2.31 |
|---|---|---|---|
| Found: | 75.17 | 6.65 | 2.50 |

EXAMPLE III (3S,5S)-3-[(tert.Butyloxycarbonyl)methyl]-5-hydroxymethyl-2-pyrrolidinone 246 g of (3S,5S)-1-(benzyloxycarbonyl)-3-[(tert.butyloxycarbonyl)methyl]-5-[(trityloxy)methyl]-2-pyrrolidinone in 1.6 liters of tert.butanol are hydrogenated for 1½ days at 50° C. under a hydrogen pressure of 5 bar with 50 g of palladium (10% on activated charcoal). Then the mixture is diluted with acetone, the catalyst is filtered off and the filtrate is evaporated down. The residue is stirred in 3 batches with a total of 2 liters of petroleum ether. The remaining oil is dried in vacuo.

Yield: 77.8 g (84% of theory), $R_f$ value: 0.43 (silica gel; ethyl acetate/methanol=15:1)

EXAMPLE IV (3S,5S)-3-[(tert.Butyloxycarbonyl)methyl]-5-[(methanesulphonyloxy)methyl]-2-pyrrolidinone To 2.7 g of (3S,5S)-3-[(tert.butyloxycarbonyl)methyl]-5-hydroxymethyl-2-pyrrolidinone in 25 ml of methylene chloride are added, at 0° C., 1.76 g of methanesulphonic acid chloride, followed by 1.7 g of triethylamine, by dropwise addition. After one hour stirring whilst cooling with ice and 2 hours stirring at ambient temperature the mixture is combined with ice water, the organic phase is separated off, washed twice with water, dried and evaporated down. After recrystallisation from ethyl acetate, 2.35 g (65% of theory) are obtained.

Melting point: 114°–116° C.

$R_f$ value: 0.47 (silica gel; toluene/acetone=1:3)

| Calculated: | C 46.89 | H 6.89 | N 4.56 | S 10.43 |
|---|---|---|---|---|
| Found: | 46.90 | 6.79 | 4.84 | 10.17 |

EXAMPLE V (3S,5S)-3-[(tert.Butyloxycarbonyl)methyl]-5-[(4'-cyano-4-biphenylyl)oxymethyl]-2-pyrrolidone 3.4 g of potassium tert.butoxide are added to 5.9 g of 4'-cyano-4-hydroxybiphenyl in 150 ml of dry dimethylformamide. After one hour stirring at ambient temperature, 9.2 g of (3S,5S)-3-[(tert.butyloxycarbonyl)methyl]-5-[(mesthanesulphonyloxy)methyl]-2-pyrrolidinone are added and the mixture is stirred for 3 days at ambient temperature. The reaction mixture is added to 500 ml of water and the mixture is stirred for half an hour. The precipitate is suction filtered and recrystallised twice from 95% ethanol.

Yield: 8.35 g (68% of theory),

Melting point: 159°–160° C.

$R_f$ value: 0.64 (silica gel; ethyl acetate)

EXAMPLE VI (3S,5S)-5-[(4'-Amidino-4-biphenyl)oxymethyl]-3-[methoxycarbonyl)methyl]-2-pyrrolidinone-hydrochloride 0.9 g of (3S,5S)-3-[(tert.butyloxycarbonyl)methyl]-5-[(4'-cyano-4-biphenylyl)oxymethyl]-2-pyrrolidinone are added to 50 ml of dry methanol, which has been saturated with hydrogen chloride gas whilst cooling with ice. The reaction mixture is covered with some petroleum ether and stirred overnight. It is concentrated by evaporation, the residue is combined with 11 ml of methanol and a pH of about 9 is achieved with conc. aqueous ammonia, whilst cooling with ice. After 3 days' stirring at ambient temperature the mixture is evaporated down, the residue is stirred with 100 ml of methylene chloride/methanol (85:15), then filtered and the filtrate is concentrated by evaporation. The residue is stirred with methylene chloride/tert.butyl-methylether and the solid matter is suction filtered and dried.

Yield: 0.8 g (87% of theory)

$R_f$ value: 0.45 (Reversed Phase silica gel (RP8); methanol/5% aqueous saline solution=3:2)

EXAMPLE VII (3S,5S)-5-[(4'-Methoxycarbonylamidino-4-biphenylyl)oxymethyl]-3-[(methoxycarbonyl)methyl]-2-pyrrolidinone To a suspension of 2.0 g of (3S,5S)-5-[(4'-amidino-4-biphenylyl)oxymethyl]-3-[(methoxycarbonyl)methyl]-2pyrrolidinone hydrochloride in 200 ml of methylene chloride are added 480 mg of methyl chloroformate and then 50 ml of 0.2 molar sodium hydroxide solution are added dropwise at ambient temperature, with vigorous stirring. The organic phase is separated off, washed twice with water, dried and evaporated down. The residue is chromatographed over a silica gel column with ethyl acetate and ethyl acetate/methanol (95:5). The product is heated to boiling with 15 ml of ethyl acetate, the suspension is cooled and the solids are suction filtered and dried.

Yield: 430 mg (21% of theory),

Melting point: 183°–184° C. (decomp.)

$R_f$ value: 0.47 (silica gel; ethyl acetate/methanol= 97:3)

| | | | |
|---|---|---|---|
| Calculated: | C 62.86 | H 5.73 | N 9.56 |
| Found: | 62.60 | 5.85 | 9.55 |

The following is obtained analogously: (1) (3S,5S)-5-[(4'-benzyloxycarbonylamidino-4-biphenylyl)oxymethyl]-3-[(methoxycarbonyl)methyl]-2-pyrrolidinone
(Carried out with benzylchloroformate in tetrahydrofuran)
$R_f$ value: 0.37 (silica gel; ethyl acetate)

EXAMPLE VIII (3S,5S)-3-Carboxymethyl-5-[(4'-methoxycarbonyl-amidino-4-biphenylyl)oxymethyl]-2-pyrrolidinone 440 mg of (3S,5S)-5-[(4'-methoxycarbonylamidino-4-biphenylyl)oxymethyl]-3-[(methoxycarbonyl)methyl]-2-pyrrolidinone are suspended in a mixture of 8 ml of tetrahydrofuran and 4 ml of water and 0.75 ml of 4N sodium hydroxide solution are added, with stirring, at ambient temperature. After 30 minutes stirring at ambient temperature the reaction mixture is acidified with glacial acetic acid and diluted with some water. The precipitate is suction filtered, washed with water and dried.

Yield: 320 mg (75% of theory)

$R_f$ value: 0.68 (Reversed Phase silica gel (RP8); methanol/5% aqueous saline solution=6:4)

The following is obtained analogously:
(1) (3S,5S)-5-[(4'-benzyloxycarbonylamidino-4-biphenylyl)oxymethyl]-3-carboxymethyl-2-pyrrolidinone Melting point: 202° C. (decomp.)

$R_f$ value: 0.44 (Reversed Phase silica gel (RP8); methanol/5% aqueous saline solution=6:4)

EXAMPLE IX (3S,5S)-5-[(4'-Amidino-4-biphenylyl)oxymethyl]-3-carboxymethyl-2-pyrrolidinone To 20 g of (3S,5S)-5-[(4'-amidino-4-biphenylyl)oxymethyl]-3-[(methoxycarbonyl)methyl]-2-pyrrolidinone-hydrochloride in 200 ml of methanol are added 37.5 ml of 4N sodium hydroxide solution and the mixture is stirred for 6 hours at ambient temperature. 10.7 g of ammonium chloride are added, followed by a further 200 ml of water after a few minutes, and the mixture is stirred for 45 minutes in an ice/water bath. The precipitate is suction filtered, washed twice each with methanol and water/methanol (2:1) and dried.

Yield: 15.2 g (86% of theory),

Melting point: 292°–294° C. (decomp.)

$R_f$ value: 0.63 (Reversed Phase silica gel (RP8); methanol/10% aqueous saline solution=6:4)

| | | | |
|---|---|---|---|
| Calculated: | C 65.38 | H 5.76 | N 11.44 |
| Found: | 65.20 | 5.80 | 11.54 |

EXAMPLE X (3S,5S)-5-[(4'-Amidino-4-biphenylyl)oxymethyl]-3-[(neopentyloxycarbonyl)methyl]-2-pyrrolidinone×1.1 HCl ×0.5 water Hydrogen chloride gas is passed, with stirring, over a suspension of 1.1 g of (3S,5S)-5-[(4'-amidino-4-biphenylyl)oxymethyl]-3-carboxymethyl-2-pyrrolidinone in 10 g of liquid neopentyl alcohol. After 20 minutes the reaction mixture is stirred for another hour at 60° C. The reaction mixture is mixed with diethylether after cooling and the precipitate is suction filtered and dried in a desiccator over potassium hydroxide and conc. sulphuric acid. The crude product is taken up in methylene chloride, with gentle heating, filtered and the filtrate is evaporated down. The residue is stirred with acetone/diethylether, suction filtered, washed with diethylether and dried over sodium hydroxide and conc. sulphuric acid in a desiccator.

Yield: 1.14 g (80% of theory), $R_f$ value: 0.24 (Reversed Phase silica gel (RP8); methanol/5% aqueous saline solution=6:4)

| | | | | |
|---|---|---|---|---|
| Calculated: | C 61.70 | H 6.86 | N 8.63 | Cl 8.01 |
| Found: | 61.98 | 7.14 | 8.43 | 7.87 |

Mass spectrum: $(M+H)^+=438$

The following are obtained analogously:

(1) (3S,5S)-5-[(4'-amidino-4-biphenylyl)oxymethyl]-3-[(isobutyloxycarbonyl)methyl]-2-pyrrolidinone-hydrochloride $R_f$ value: 0.26 (Reversed Phase silica gel (RP8); methanol/5% aqueous saline solution=6:4)

Mass spectrum: $(M+H)^+=424$ (2) (3S,5S)-5-[(4'-amidino-4-biphenylyl)oxymethyl]-3-[(benzyloxycarbonyl)methyl]-2-pyrrolidinone×1.05 HCl×0.5 water $R_f$ value: 0.19 (Reversed Phase silica gel (RP8); methanol/5% aqueous saline solution=6:4)

| | | | | |
|---|---|---|---|---|
| Calculated: | C 64.24 | H 5.80 | N 8.32 | Cl 7.37 |
| Found: | 64.38 | 5.73 | 8.20 | 7.42 |

Mass spectrum: $(M+H)^+=458$ (3) (3S,5S)-5-[(4'-amidino-4-biphenylyl)oxymethyl]-3-[(ethyloxycarbonyl)methyl]-2-pyrrolidinone-hydrochloride $R_f$ value: 0.54 (Reversed Phase silica gel (RP8);

methanol/10% aqueous saline solution=6:4)

(4) (3S,5S)-5-[(4'-amidino-4-biphenylyl)oxymethyl]-3-[(isopropyloxycarbonyl)methyl]-2-pyrrolidinone-hydrochloride $R_f$ value: 0.49 (Reversed Phase silica gel (RP8); methanol/10% aqueous saline solution=6:4)

(5) (3S,5S)-5-[(4'-amidino-4-biphenylyl)oxymethyl]-3-[(propyloxycarbonyl) methyl]-2-pyrrolidinone-hydrochloride

EXAMPLE 1

(3S,5S)-5-[(4'Acetoxymethyloxycarbonylamidino-4-biphenylyl)oxymethyl]3[(methoxycarbonyl)methyl]-2-pyrrolidinone 1.06 g of (3S,5S)-5-[(4'-amidino-4-biphenylyl)oxymethyl]-3-[(methoxycarbonyl)methyl]-2-pyyrolidinonehydrochloride, 800 mg of acetoxymethyl-(4nitrophenyl)carbonate and 726 mg of N-ethyl-diisopropylamine are stirred in 80 ml of methylene chloride for 20 hours at ambient temperature. The reaction mixture is washed with water, with 40 ml of 0.1N sodium hydroxide solution and again with water. Then the organic phase is separated off, dried and evaporated down. The residue is chromatographed over a silica gel column with methylene chloride/methanol (97:3). The product is briefly stirred with tert.butylmethylether in the warm, then suction filtered and dried.

Yield: 380 mg (30% of theory), $R_f$ value: 0.25 (silica gel; methylene chloride/methanol =95:5)

| Calculated: | C 60.36 | H 5.47 | N 8.45 |
|---|---|---|---|
| Found: | 60.33 | 5.87 | 8.07 |

Mass spectrum: $(M+H)^+=498$

The following are obtained analogously:

(1) (3S,5S)-5-[[4'-(1-acetoxyethyl)oxycarbonylamidino-4-biphenylyl]oxymethyl]-3-[(methoxycarbonyl) methyl]-2-pyrrolidinone ×0.75 water $R_f$ value: 0.36 (silica gel; methylene chloride/acetone= 65:35)

| Calculated: | C 59.48 | H 5.86 | N 8.00 |
|---|---|---|---|
| Found: | 59.38 | 5.73 | 8.02 |

Mass spectrum: $(M+H)^+=512$ (2) (3S,5S)-5-[[4'-(1-acetoxyethyl)oxycarbonylamidino-4-biphenylyl]oxymethyl]-3-[(ethoxycarbonyl)methyl]-2-pyrrolidinone (3) (3S,5S)-5-[(4'-acetoxymethyloxycarbonylamidino-4-biphenylyl) oxymethyl]-3-[(ethoxycarbonyl) methyl]-2-pyrrolidinone (4) (3S,5S)-5-[(4'-acetoxymethyloxycarbonylamidino-4-biphenylyl)oxymethyl]-3-[(isopropoxycarbonyl)methyl]-2-pyrrolidinone (5) (3S,5S)-5-[(4'-acetoxymethyloxycarbonylamidino-4-biphenylyl)oxymethyl]-3-[(benzyloxycarbonyl)methyl]-2-pyrrolidinone (6) (3S,5S)-3-[(methoxycarbonyl)methyl]-5-[(4'-pivaloyloxymethyloxycarbonylamidino-4-biphenylyl)-oxymethy]-2-pyrrolidinone (7) (3S,5S)-3-[(ethoxycarbonyl)methyl]-5-[(4'-pivaloyloxymethyloxycarbonylamidino-4-biphenylyl)-oxymethy]-2-pyrrolidinone (8) (3S,5S)-5-[(4'-butyryloxymethyloxycarbonylamidino-4-biphenylyl)oxymethyl]-3-[(methoxycarbonyl)methyl]-2-pyrrolidinone (9) (3S,5S)-5-[(4'-acetoxymethyloxycarbonylamidino-4-biphenylyl)oxymethyl]-3-[(propoxycarbonyl)methyl]-2-pyrrolidinone

(10) (3S,5S)-5-[(4'-acetoxymethyloxycarbonylamidino-4-biphenylyl)oxymethyl]-3-[(pivaloyloxymethyloxycarbonyl)methyl]-2-pyrrolidinone

(11) (3S,5S)-5-[(4'-acetoxymethyloxycarbonylamidino-4-biphenylyl)sulphonylmethyl]-3-[(methoxycarbonyl)methyl]-1-(3-phenylpropyl)-2-pyrrolidinone

(12) (3S,5S)-3-[(cyclohexyloxycarbonyl)methyl]-5-[(4'-propionyloxymethyloxycarbonylamidino-4-biphenylyl)oxymethyl]-2-pyrrolidinone

(13) (3S,5S)-5-[(4'-isobutyryloxymethyloxycarbonyl-amidino-4-biphenylyl)oxymethyl]-3-[(methoxycarbonyl)methyl]-2-pyrrolidinone

(14) (3S,5S)-5-[(4'-acetoxymethyloxycarbonylamidino-4-biphenylyl)oxymethyl]-3-[(neopentyloxycarbonyl)methyl]-2-pyrrolidinone

(15) (3S,5S)-5-[(4'-acetoxymethyloxycarbonylamidino-4-biphenylyl)oxymethyl]-3-[(isobutyloxycarbonyl)methyl]-2-pyrrolidinone

EXAMPLE 2

(3S,5S)-5-[(4'-Benzyloxycarbonylamidino-4-biphenylyl)-oxymethyl]-3-[[[1-(cyclohexyloxy-carbonyloxy)ethyl]oxycarbonyl]methyl]-2-pyrrolidinone 900 mg of (3S,5S)-5-[(4'-benzyloxycarbonylamidino-4-biphenylyl)oxymethyl]-3-carboxymethyl-2-pyrrolidinone, 750 mg of (1-chloroethyl)-cyclohexylcarbonate, 500 mg of potassium carbonate and a spatula tip of sodium iodide are stirred in 8 ml of dimethylsulphoxide at ambient temperature for 3 days. The mixture is combined with ice water and the precipitate is suction filtered and washed with water. The moist precipitate is taken up in ethyl acetate, dried with magnesium sulphate, filtered and concentrated by rotary evaporation. The residue is stirred with diethylether, the solid product is suction filtered, washed with diethylether and dried.

Yield: 1.5 g (95% of theory), $R_f$ value: 0.60 (silica gel; methylene chloride/acetone= 65:35)

The following are obtained analogously:

(1) (3S,5S)-5-[(4'-benzyloxycarbonylamidino-4-biphenylyl)oxymethyl]-3-[[[1-(ethyloxycarbonyloxy)ethyl]oxycarbonyl]methyl]-2-pyrrolidinone $R_f$ value: 0.43 (silica gel; methylene chloride/acetone= 65:35)

(2) (3S,5S)-5-[(4'-benzyloxycarbonylamidino-4-biphenylyl)oxymethyl]-3-[(pivaloyloxymethyloxycarbonyl)methyl]-2-pyrrolidinone $R_f$ value: 0.52 (silica gel; methylene chloride/acetone= 65:35)

(3) (3S,5S)-3-[(acetoxymethyloxycarbonyl)methyl]-5-[(4'-benzyloxycarbonylamidino-4-biphenylyl)oxymethyl]-2-pyrrolidinone (4) (3S,5S)-5-[(4'-benzyloxycarbonylamidino-4-biphenylyl)oxymethyl]-3-[(butyryloxymethyloxycarbonyl)methyl]-2-pyrrolidinone (5) (3S,5S)-5-[(4'-benzyloxycarbonylamidino -4-biphenylyl)oxymethyl]-3-[(isobutyryloxymethyloxy-carbonyl)methyl]-2-pyrrolidinone (6) (3S,5S)-3-[[(1-acetoxyethyl)oxycarbonyl]methyl]-5-[(4'-benzyloxycarbonylamidino-4-biphenylyl)oxymethyl]-2-pyrrolidinone (7) (3S,5S)-3-[(benzoyloxymethyloxycarbonyl)methyl]-5-[(4'-benzyloxycarbonylamidino-4-biphenylyl)oxymethyl]-2-pyrrolidinone (8) (3S,5S)-5-[(4'-benzyloxycarbonylamidino-4-biphenylyl)oxymethyl]-3-[[(cyclohexyloxycarbonyloxy)methyloxycarbonyl]methyl]-2-pyrrolidinone (9) (3S,5S)-5-[(4'-benzyloxycarbonylamidino-4-biphenylyl)oxymethyl]-3-[[(cyclopentyloxycarbonyloxy)methyloxycarbonyl]methyl]-2-pyrrolidinone

(10) (3S,5S)-5-[(4'-benzyloxycarbonylamidino-4-biphenylyl)oxymethyl]-1-phenyl-3-[(pivaloyloxymethyloxycarbonyl)-methyl]-2-pyrrolidinone

(11) (3S,5S)-1-benzyl-5-[(4'-benzyloxycarbonylamidino-4-biphenylyl)oxymethyl]-3-[(pivaloyloxymethyloxycarbonyl)methyl]-2-pyrrolidinone

(12) (3S,5S)-5-[(4'-benzyloxycarbonylamidino-4-biphenylyl)oxymethyl]-1-[2-(3,4-dimethoxyphenyl)ethyl]-3 [(pivaloyloxymethyloxycarbonyl)methyl]-2-pyrrolidinone

(13) (3S,5S)-5-[(4'-benzyloxycarbonylamidino-4-biphenylyl)oxymethyl]-1-(2-methoxyethyl)-3-[(pivaloyloxymethyloxycarbonyl)methyl]-2-pyrrolidinone

(14) (3S,5S)-5-[(4'-benzyloxycarbonylamidino-4-biphenylyl)oxymethyl]-1-[(morpholino-N-carbonyl)methyl]-3-[(pivaloyloxymethyloxycarbonyl)methyl]-2-pyrrolidinone

(15) (3S,5S)-1-acetyl-5-[(4'-benzyloxycarbonylamidino-4-biphenylyl)oxymethyl]-3-[[[1-(ethyloxycarbonyloxy)ethyl]oxycarbonyl]methyl]-pyrrolidine

(16) (3S,5S)-5-[(4'-benzyloxycarbonylamidino-4-biphenylyl)oxymethyl]-3-[[[1-(ethyloxycarbonyloxy)ethyl]oxycarbonyl]methyl]-1-methanesulphonylpyrrolidine

(17) (3S,5S)-1-benzoyl-5-[(4'-benzyloxycarbonylamidino-4-biphenylyl)oxymethyl]-3-[[[1-(ethyloxycarbonyloxy)ethyl]oxycarbonyl]methyl]-pyrrolidine

(18) (3S,5S)-5-[(4'-benzyloxycarbonylamidino-4-biphenylyl)oxymethyl]-3-[[[1-(pivaloyloxy)butyl]oxycarbonyl]methyl]-2-pyrrolidinone

(19) (3S,5S)-5-[(4'-benzyloxycarbonylamidino-4-biphenylyl)oxymethyl]-3-[[[l(butyloxycarbonyloxy)ethyl]oxycarbonyl]methyl]-2-pyrrolidinone

(20) (3S,5S)-5-[(4'-benzyloxycarbonylamidino-4-biphenylyl)oxymethyl]-3-[[(cyclohexylcarbonyloxymethyl)oxycarbonyl]methyl]-2-pyrrolidinone

(21) (3R,S;4R,S)-4-[(4'-benzyloxycarbonylamidino-4-biphenylyl)oxymethyl]-3-methyl-3-[(pivaloyloxymethyloxycarbonyl)methyl]-2-pyrrolidinone

(22) (3R,S;4R,S)-4-[(4'-benzyloxycarbonylamidino-4-biphenylyl)carbonylaminomethyl]-3-[[[1-(ethyloxycarbonyloxy)ethyl]oxycarbonyl]methyl]-2-pyrrolidinone

(23) (3S,5S)-5-[(4'-benzyloxycarbonylamidino-3-fluoro-4-biphenylyl)oxymethyl]-3-[(pivaloyloxymethyloxycarbonyl)methyl]-2-pyrrolidinone

(24) (3S,5S)-5-[(7-benzyloxycarbonylamidino-9,10-dihy- 2-phenanthrenyl)oxymethyl]-3-[[[1-(cyclohexyloxycarbonyloxy)ethyl]oxycarbonyl]methyl]-2-pyrrolidinone

(25) (3S,5S)-5-[(7-benzyloxycarbonylamidino-2-fluorenyl)oxymethyl]-3-[(pivaloyloxymethyloxycarbonyl)methyl]-2-pyrrolidinone

(26) (3S,5S)-5-[(4'-methoxycarbonylamidino-4-biphenylyl)oxymethyl]-3-[(pivaloyloxymethyloxycarbonyl)methyl]-2-pyrrolidinone×0.5 water $R_f$ value: 0.35 (silica gel; methylene chloride/acetone= 65:35)

| | | | |
|---|---|---|---|
| Calculated: | C 61.30 | H 6.25 | N 7.66 |
| Found: | 61.40 | 6.20 | 7.38 |

Mass spectrum: $(M+H)^+=540$

(27) (3S,5S)-3-[[[1-(ethyloxycarbonyloxy)ethyl]oxycarbonyl]methyl]-5-[(4'-methoxycarbonylamidino-4-biphenylyl) oxymethyl]-2-pyrrolidinone

(28) (3S,5S)-3-[[[1-(cyclohexyloxycarbonyloxy)ethyl]oxycarbonyl]methyl]-5-[(4'-methoxycarbonylamidino-4-biphenylyl)oxymethyl]-2-pyrrolidinone

(29) (3S,5S)-5-[(4'-ethoxycarbonylamidino-4-biphenylyl)oxymethyl]-3-[(pivaloyloxymethyloxycarbonyl)methyl]-2-pyrrolidinone

(30) (3S,5S)-5-[(4'-benzyloxycarbonylamidino-4-biphenylyl)oxymethyl]-3-[[[1-(propionyloxy)ethyl]oxycarbonyl]methyl]-2-pyrrolidinone

(31) (3S,5S)-5-[(4'-benzyloxycarbonylamidino-4-biphenylyl)oxymethyl]-3-[[[1-(cycloheptyloxycarbonyloxy)ethyl]oxycarbonyl]methyl]-2-pyrrolidinone

(32) (3S,5S)-5-[(4'-benzyloxycarbonylamidino-4-bi-phenylyl)oxymethyl]-3-[[[1-(isopropyloxycarbonyloxy)ethyl]oxycarbonyl]methyl]-2-pyrrolidinone

(33) (3S,5S)-5-[(4'-benzyloxycarbonylamidino-4-biphenylyl)oxymethyl]-3-[[[1-(isobutyloxycarbonyloxy)ethyl]oxycarbonyl]methyl]-2-pyrrolidinone

(34) (3S,5S)-5-[(4'-benzyloxycarbonylamidino-4-biphenylyl)oxymethyl]-3-[[[1-(tert.butyloxycarbonyloxy)ethyl]oxycarbonyl]methyl]-2-pyrrolidinone

(35) (3S,5S)-5-[(4'-benzyloxycarbonylamidino-4-biphenylyl)oxymethyl]-3-[[[1-(propyloxycarbonyloxy)ethyl]oxycarbonyl]methyl]-2-pyrrolidinone

EXAMPLE 3

(3S,5S)-5-[(4'-Amidino-4-biphenylyl)oxymethyl]-3-[[[1-(cyclohexyloxycarbonyl)ethyl]oxycarbonyl]methyl]-2-pyrrolidinone ×1.1 HCl×0.5 water 1.1 g of (3S,5S)-5-[(4'-benzyloxycarbonylamidino-4-biphenylyl)oxymethyl]-3-[[[1-(cyclohexyloxycarbonyloxy)ethyl]oxycarbonyl]methyl]-2-pyrrolidinone, dissolved in 10 ml of dimethylformamide, are mixed with 3.26 ml of 0.5N hydrochloric acid and hydrogenated with 0.2 g of palladium on charcoal (10% palladium) at ambient temperature under a hydrogen pressure of 3.4 bar. After 2½ hours the mixture is suction filtered, the filtrate is combined with saturated saline solution and extracted three times with tetrahydrofuran. The combined organic phases are washed with saturated saline solution, filtered and evaporated down. The residue is stirred with diethylether and the supernatant solution is decanted off. The residue is dried in the desiccator over concentrated sulphuric acid and potassium hydroxide.

Then it is triturated with diethylether, suction filtered, washed with diethylether and dried.

Yield: 700 mg (75% of theory), $R_f$ value: 0.16 (Reversed Phase silica gel (RP8); methanol/5% aqueous saline solution=6:4)

| Calculated: | C 59.37 | H 6.37 | N 7.16 | Cl 6.65 |
|---|---|---|---|---|
| Found: | 58.94 | 6.45 | 7.14 | 6.77 |

Mass spectrum: $(M+H)^+=538$

The following are obtained analogously:

(1) (3S,5S)-5-[(4'-amidino-4-biphenylyl)oxymethyl]-3-[[1-(ethyloxycarbonyloxy)ethyl]oxycarbonyl]methyl]-2-pyrrolidinone ×1.05 HCl×0.5 water $R_f$ value: 0.34 (Reversed Phase silica gel (RP8); methanol/5% aqueous saline solution=6:4)

| Calculated: | C 56.57 | H 5.90 | N 7.92 | Cl 7.01 |
|---|---|---|---|---|
| Found: | 56.51 | 5.93 | 7.88 | 7.10 |

Mass spectrum: $(M+H)^+=484$ (2) (3S,5S)-5-[(4'-amidino-4-biphenylyl)oxymethyl]-3-[(pivaloyloxymethyloxycarbonyl)methyl]-2-pyrrolidinone× 1.1 HCl×0.5 water $R_f$ value: 0.30 (Reversed Phase silica gel (RP8); methanol/5% aqueous saline solution=6:4)

| Calculated: | C 58.85 | H 6.29 | N 7.92 | Cl 7.35 |
|---|---|---|---|---|
| Found: | 58.69 | 6.21 | 7.75 | 7.40 |

Mass spectrum: $(M+H)^+=482$ (3) (3S,5S)-3-[(acetoxymethyloxycarbonyl)methyl]-5-[(4'-amidino-4-biphenylyl)oxymethyl]-2-pyyrolidinonehydrochloride (4) (3S,5S)-5-[(4'-amidino-4-biphenylyl) oxymethyl]-3-[(butyryloxymethyloxycarbonyl)methyl]-2-pyyrolidinonehydrochloride (5) (3S,5S)-5-[(4'-amidino-4-biphenylyl)oxymethyl]-3-[(isobutyryloxymethyloxycarbonyl)methyl]-2-pyyrolidinonehydrochloride (6) (3S,5S)-3-[[(1-acetoxyethyl)oxycarbonyl]methyl]-5-[(4'-amidino-4-biphenylyl)oxymethyl]-2-pyyrolidinonehydrochloride (7) (3S,5S)-5-[(4'-amidino-4-biphenylyl)oxymethyl]-3-[(benzoyloxymethyloxycarbonyl)methyl]-2-pyyrolidinonehydrochloride (8) (3S,5S)-5-[(4'-amidino-4-biphenylyl)oxymethyl]-3-[(cyclohexyloxycarbonyloxy) methyloxycarbonyl]methyl]-2-pyyrolidinonehydrochloride (9) (3S,5S)-5-[(4-amidino-4-biphenylyl)oxymethyl]-3-[(cyclopentyloxycarbonyloxy) methyloxycarbonyl]methyl]-2-pyyrolidinonehydrochloride

(10) (3S,5S)-5-[(4'-amidino-4-biphenylyl)oxymethyl]-1-phenyl-3-[(pivaloyloxymethyoxycarbony)methyl]-2-pyyrolidinonehydrochloride

(11) (3S,5S)-5-[(4'-amidino-4-biphenylyl)oxymethyl]-1-benzyl-3-[(pivaloyloxymethyloxycarbonyl)methyl]-2-pyyrolidinonehydrochloride

(12) (3S,5S)-5-[(4'-amidino-4-biphenylyl)oxymethyl]-1-[2-(3,4-dimethoxyphenyl)ethyl]-3-[(pivaloyloxymethyloxycarbonyl 1) methyl]-2-pyrrolidinonehydrochloride

(13) (3S,5S)-5-[(4'-amidino-4-biphenylyl)oxymethyl]-1-(2-methoxyethyl)-3-[(pivaloyloxymethyloxycarbonyl)-methyl]-2-pyrrolidinonehydrochloride

(14) (3S,5S)-5-[(4'-amidino-4-biphenylyl)oxymethyl]-1-[(morpholino-N-carbonyl) methyl]-3-[(pivaloyloxymethyloxycarbonyl)methyl]-2-pyrrolidinonehydrochloride

(15) (3S,5S)-1-acetyl-5-[(4'-amidino-4-biphenylyl)oxymethyl]-3-[[[1-(ethyloxycarbonyloxy)ethyl]oxycarbonyl]methyl]pyrrolidinehydrochloride

(16) (3S,5S)-5-[(4'-amidino-4-biphenylyl)oxymethyl]-3-[[[1-(ethyloxycarbonyloxy)ethyl]oxycarbony]methy]-1-methanesulphonylpyrrodinehydrochloride

(17) (3S,5S)-5-[(4'-amidino-4-biphenylyl)oxymethyl]-1-benzoyl-3-[[[1-(ethyloxycarbonyloxy)ethyl]oxycarbonyl]methyl]pyrrolidinehydrochloride

(18) (3S,5S)-5-[(4'-amidino-4-biphenylyl)oxymethyl]-3-[[1(pivaloyloxy)butyl]oxycarbonylmethyl]-2-pyrrolidinonehydrochloride

(19) (3S,5S)5-[(4'-amidino-4-biphenylyl)oxymethyl]-3-[[1-(butyloxycarbonyloxy)ethyl]oxycarbonyl]methyl]-2-pyrrolidinonehydrochloride

(20) (3S,5S) 5[(4'-amidino-4-biphenylyl)oxymethyl]-3-[[(cyclohexylcarbonyloxymethyl) oxycarbonyl]methyl]-2-pyrrolidinonehydrochloride

(21) (3R, S;4R,S)-4-[(4'-amidino-4-biphenylyl)oxymethyl]-3-methyl-3-[(pivaloyloxymethyloxycarbonyl-)methyl]-2-pyrrolidinonehydrochloride

(22) (3R,S;4R,S)-4-[(4'-amidino-4-biphenylyl)carbonylaminomethyl]-3-[[[1-(ethyloxycarbonyloxy)ethyl]oxycarbonyl]methyl]-2-pyrrolidinonehydrochloride

(23) (3S,5S)-5-[(4'-amidino-3-fluoro-4-biphenylyl)oxymethyl]-3-[(pivaloyloxymethyloxycarbonyl)methyl]-2-pyrrolidinonehydrochloride

(24) (3S,5S)-5-[(7-amidino-9,10-dihydro-2-phenanthrenyl)oxymethyl]-3-[[[1-(cyclohexyloxycarbonyloxy) ethyl] oxycarbonyl]methyl]-2-pyrrolidinonehydrochloride

(25) (3S,5S)-5-[(7-amidino-2-fluorenyl)oxymethyl]-3-[(pivaloyloxymethyloxycarbonyl)methyl]-2-pyrrolidinonehydrochloride

(26) (3S,5S)-5-[(4'-amidino-4-biphenylyl)oxymethyl]-3-[[1-(propionyloxy)ethyl]oxycarbonyl]methyl]-2pyrrolidinonehydrochloride

(27) (3S,5S)-5-[(4'-amidino-4-biphenylyl)oxymethyl]-3-[[[1-(cycloheptyloxycarbonyloxy)ethyl]oxycarbonyl]methyl]-2-pyrrolidinonehydrochloride

(28) (3S,5S)-5-[(4'-amidino-4-biphenylyl)oxymethyl]-3-[[[1-(isopropyloxycarbonyloxy)ethyl]oxycarbonyl]-methyl]-2-pyrrolidinonehydrochloride

(29) (3S,5S)-5-[(4'-amidino-4-biphenylyl)oxymethyl]-3-[[[1-(isobutyloxycarbonyloxy)ethyl]oxycarbonyl]-methyl]-2-pyrrolidinonehydrochloride

(30) (3S,5S)-5-[(4'-amidino-4-biphenylyl)oxymethyl]-3-[[[1-(tert.butyloxycarbonyloxy)ethyl]oxycarbonyl]-methyl]-2-pyrrolidinonehydrochloride

(31) (3S,5S)-5-[(4'-amidino-4-biphenylyl)oxymethyl]-3-[[[1-(propyloxycarbonyloxy)ethyl]oxycarbonyl]methy]-2-pyrrolidinonehydrochloride

EXAMPLE 4

(3S,5S)-5-[(4'-Amidino-4-biphenylyl)oxymethyl]-3-[(cyclohexyloxycarbonyl)methyl]-2-pyrrolidinone×1.05 HCl×0.5 water Hydrogen chloride gas is passed, with stirring, over a suspension of 1.5 g of (3S,5S)-5-[(4'-amidino-4-biphenylyl)oxymethyl]-3-carboxymethyl-2-pyrrolidinone in 15 ml of cyclohexanol. The reaction mixture is then stirred for 2 hours at 70° C., during which time hydrogen chloride gas is passed over it from time to time. The reaction mixture is cooled, mixed with ether, the precipitate is suction filtered and dried in the desiccator over potassium hydroxide and conc. sulphuric acid. The crude product is taken up in 400 ml of methylene chloride, filtered and concentrated by evaporation. The residue is stirred with acetone/diethylether, suction filtered, washed with diethylether and dried in the desiccator and in the drying cupboard at 40° C.

Yield: 1.7 g (85% of theory), $R_f$ value: 0.26 (Reversed Phase silica gel (RP8); methanol/5% aqueous saline solution=6:4)

| Calculated: | C 62.85 | H 6.70 | N 8.46 | Cl 7.49 |
|---|---|---|---|---|
| Found: | 62.88 | 6.76 | 8.45 | 7.52 |

Mass spectrum: $(M+H)^+=450$

The following are obtained analogously:

(1) (3S,5S)-5-[(4'-amidino-4-biphenylyl)oxymethyl]-3-[(cyclohexylmethyloxycarbonyl)methyl]-2-pyrrolidinone×1.08 HCl×0.5 water $R_f$ value: 0.18 (Reversed Phase silica gel (RP8); methanol/5% aqueous saline solution=6:4)

| Calculated: | C 63.34 | H 6.91 | N 8.21 | Cl 7.48 |
|---|---|---|---|---|
| Found: | 63.16 | 7.01 | 8.29 | 7.61 |

Mass spectrum: $(M+H)^+=464$ (2) (3S,5S)-5-[(4'-amidino-4-biphenylyl)oxymethyl]-3-[(cyclopentyloxycarbonyl)methyl]-2-pyrrolidinone×1.05 HCl×0.5 water $R_f$ value: 0.27 (Reversed Phase silica gel (RP8); methanol/5% aqueous saline solution=6:4)

| Calculated: | C 62.19 | H 6.48 | N 8.70 | Cl 7.71 |
|---|---|---|---|---|
| Found: | 62.05 | 6.70 | 8.82 | 7.79 |

Mass spectrum: $(M+H)^+=436$ (3) (3S,5S)-5-[(4'-amidino-4-biphenylyl)oxymethyl]-3-[(cycloheptyloxycarbonyl)methyl]-2-pyrrolidinone×1.1 HCl×1 water $R_f$ value: 0.16 (Reversed Phase silica gel (RP8); methanol/5% aqueous saline solution=6:4)

| Calculated: | C 62.16 | H 6.97 | N 8.05 | Cl 7.48 |
|---|---|---|---|---|
| Found: | 62.33 | 7.15 | 7.96 | 7.63 |

(4) (3S,5S)-5-[(4'-amidino-4-biphenylyl)oxymethyl]-3-[(cyclooctyloxycarbonyl)methyl]-2-pyrrolidinonehydrochloride (5) (3S,5S)-5-[(4'-amidino-4-biphenylyl)oxymethyl]-3-[[(N-methylpiperidin-4-yl)oxycarbonyl]methyl]-2-pyrrolidinonedihydrochloride (6) (3S,5S)-5-[(4'-amidino-4-biphenylyl)oxymethyl]-3-[[(tetrahydrofuran-2-yl)methyl]oxycarbonyl]methyl]-2-pyrrolidinonehydrochloride (7) (3S,5S)-5-[(4'-amidino-4-biphenylyl) oxymethyl]-3-[[2-(cyclohexyl)ethyl]oxycarbonyl]methyl]-2-pyrrolidinonehydrochloride (8) (3S,5S)-5-[(4'-amidino-4-biphenylyl)oxymethyl]-3-[[ [(2-cyclopentylmethyl) oxycarbonyl]methyl]-2-pyrrolidinonehydrochlride (9) (3S,5S)-5-[(4'-amidino-4-biphenylyl)oxymethyl]-3-[ [(cycloheptylmethyl)oxycarbonyl]methyl]-2-pyrrolidinonehydrochloride

(10) (3S,5S)-5-[(4'-amidino-4-biphenylyl)oxymethyl]-3-[ [(N-methylpiperidin-3-yl)oxycarbonyl]methyl]-2-pyrrolidinonedihydrochloride

(11) (3S,5S)-5-[(4'-amidino-4-biphenylyl)oxymethyl]-3-[ [(N-ethylpiperidin-4-yl) oxycarbonyl]methyl]-2-pyrrolidinonedihydrochloride

(12) (3S,5S)-5-[(4'-amidino-4-biphenylyl)oxymethyl]-3-[ [[(N-methylpyrrolidin-2-yl)methyl]oxycarbonyl]methyl]-2-pyrrolidinonedihydrochloride

(13) (3S,5S)-5-[(4'-amidino-4-biphenylyl)oxymethyl]-3-[ [(tetrahydrofuran-3-yl)oxycarbonyl]methyl]-2-pyrrolidinonehydrochloride

(14) (3S,5S)-5-[(4'-amidino-4-biphenylyl)oxymethyl]-3-[ [(2-methylcyclohexyl)oxycarbonyl]methyl]-2-pyrrolidinonehydrochloride

(15) (3S,5S)-5-[(4'-Amidino-4-biphenylyl)oxymethyl]-3-[[(3-methylcyclohexyl)oxycarbonyl]methyl]-2-pyrrolidinonehydrochloride

(16) (3S,5S)-5-[(4'-amidino-4-biphenylyl)oxymethyl]-3-[ [(4-methylcyclohexyl)oxycarbonyl]methyl]-2-pyrrolidinonehydrochloride

(17) (3S,5S)-5-[(4'-amidino-4-biphenylyl)oxymethyl]-3-[ [(3,5-dimethylcyclohexyl)oxycarbonyl]methyl]-2-pyrrolidinonehydrochloride

(18) (3S,5S)-5-[(4'-amidino-4-biphenylyl)oxymethyl]-3-[ [(3,3,5-trimethylcyclohexyl)oxycarbonyl]methyl]-2-pyrrolidinonehydrochloride

(19) (3S,5S)-5-[(4'-amidino-4-biphenylyl)oxymethyl]-3-[ [(3,3,5,5-tetramethylcyclohexyl)oxycarbonyl]methyl]-2-pyrrolidinonehydrochloride

(20) (3S,5S)-5-[(4'-amidino-4-biphenylyl)oxymethyl]-3-[ [(4-ethylcyclohexyl)oxycarbonyl]methyl]-2-pyrrolidinonehydrochloride

(21) (3S,5S)-5-[(4'-amidino-4-biphenylyl)oxymethyl]-3-[ [(4-isopropylcyclohexyl)oxycarbonyl]methyl]-2-pyrrolidinonehydrochloride

(22) (3S,5S)-5-[(4'-amidino-4-biphenylyl)oxymethyl]-3-[ [(4-tert.butylcyclohexyl)oxycarbonyl]methyl]-2-pyrrolidinonehydrochloride

(23) (3S,5S)-5-[(4'-amidino-4-biphenylyl)oxymethyl]-3-[(methyloxycarbonyl) methyl]-2-pyrrolidinonehydrochloride

(24) (3S,5S)-5-[(4'-amidino-4-biphenylyl)oxymethyl]-3-[ [(4-methoxycyclohexyl)oxycarbonyl]methyl]-2-pyrrolidinonehydrochloride

(25) (3S,5S)-5-[(4'-amidino-4-biphenylyl)oxymethyl]-3-[ [(4-ethoxycyclohexyl)oxycarbonyl]methyl]-2-pyrrolidinonehydrochloride

(26) (3S,5S)-5-[(4'-amidino-4-biphenylyl)oxymethyl]-3-[ [(4-dimethylaminocyclohexyl)oxycarbonyl]methyl]-2-pyrrolidinonedihydrochloride

(27) (3S,5S)-5-[(4'-amidino-4-biphenylyl)oxymethyl]-3[ [(4-trifluoromethylcyclohexyl)oxycarbonyl]methyl]-2-pyrrolidinonehydrochloride

(28) (3S,5S)-5-[(4'-amidino-4-biphenylyl) oxymethyl]-3-[[[(3-methylnorbornan-2-yl) methyl]oxycarbonyl]methyl]-2-pyrrolidinonehydrochloride

(29) (3S,5S)-5-[(4'-amidino-4-biphenylyl)oxymethyl]-3-[ [(2-norbornyl)oxycarbonyl]methyl]-2-pyrrolidinonehydrochloride

(30) (3S,5S)-5-[(4'-amidino-4-biphenylyl)oxymethyl]-3-[(myrtanyloxycarbonyl)methyl]-2-pyrrolidinonehydrochloride

(31) (3S,5S)-5-[(4'-amidino-4-biphenylyl)oxymethyl]-3-[[[2-(6,6-dimethyl-bicyclo[3.1.1]hept-2-yl)ethyl]oxycarbonyl]methyl]-2-pyrrolidinonehydrochloride

(32) (3S,5S)-5-[(4'-amidino-4-biphenylyl)oxymethyl]-3-[(cinnamyloxycarbonyl)methyl]-2-pyrrolidinonehydrochloride

(33) (3S,5S)-5-[(4'-amidino-4-biphenylyl)oxymethyl]-3-[[(2-indanyl)oxycarbonyl]methyl]-2-pyrrolidinonehydrochloride

EXAMPLE 5

(3S,5S)-3-[(Cyclohexyloxycarbonyl)methyl]-5-[(4'-methoxycarbonylamidino-4-biphenylyl)oxymethyl]-2-pyrrolidinone To a mixture of 1.1 g of (3S,5S)-5-[(4'-amidino-4-biphenylyl)oxymethyl]-3-[(cyclohexyloxycarbonyl)methyl]2-pyrrolidinone×1.05 HCl×0.5 water in 30 ml of tetrahydrofuran and 5 ml of water are added 0.2 ml of methylchloroformate and then 9.6 ml of 0.5N sodium hydroxide solution are added dropwise with stirring. The reaction mixture is evaporated down, mixed with ice water and the solid matter is suction filtered and dried. After chromatography over a silica gel column with ethyl acetate, a solid substance is obtained which is boiled with 20 ml of ethyl acetate. After cooling, the mixture is suction filtered, washed with diethylether and dried.

Yield: 570 mg (50% of theory), $R_f$ value: 0.27 (silica gel; ethyl acetate)

| | | | |
|---|---|---|---|
| Calculated: | C 66.26 | H 6.55 | N 8.28 |
| Found: | 65.96 | 6.54 | 8.37 |

Mass spectrum: $(M+H)^+=508$

The following are obtained analogously:

(1) (3S,5S)-3-[(cyclohexylmethyloxycarbonyl)methyl]-5-[(4'-ethoxycarbonylamidino-4-biphenylyl)oxymethyl]2-pyrrolidinone (2) (3S,5S)-3-[(cyclopentyloxycarbonyl)methyl]-5-[(4'-methoxycarbonylamidino-4-biphenylyl)oxymethyl]-2-pyrrolidinone (3) (3S,5S)-3-[(cycloheptyloxycarbonyl)methyl]-5-[(4'-methoxycarbonylamidino-4-biphenylyl) oxymethyl]-2-pyrrolidinone (4) (3S,5S)-3-[(cyclooctyloxycarbonyl)methyl]-5-[(4'-methoxycarbonylamidino-4-biphenylyl)oxymethyl]-2-pyrrolidinone

EXAMPLE 6

(3S,5S)-5-[[4,(O,O'-Diethylphosphono)amidino-4-biphenylyl]oxymethyl]-3-[(methoxycarbonyl)methyl]-2-pyrrolidinone To a mixture of 1.1 g of (3S,5S)-5-[(4'-amidino-4-biphenylyl)oxymethyl]-3-[(methoxycarbonyl)methyl]-2-pyrrolidinone-toluenesulphonate in 20 ml of tetrahydrofuran and 2 ml of water are added 380 mg of diethylphosphate chloride and then 8.4 ml of 0.5N sodium hydroxide solution are added dropwise, with stirring. Some more diethylphosphate chloride and sodium hydroxide solution are added and the mixture is stirred again. The organic solvent is removed by rotary evaporation, the aqueous phase is decanted off and the oily residue is purified by chromatography over a silica gel column with methylene chloride/methanol (95:5).

Yield: 0.47 g (45% of theory), $R_f$ value: 0.13 (Reversed Phase silica gel (RP8); methanol/5% aqueous saline solution=6:4)

| | | | |
|---|---|---|---|
| Calculated: | C 58.02 | H 6.23 | N 8.12 |
| Found: | 57.88 | 6.42 | 8.30 |

Mass spectrum: $M^+=517$

EXAMPLE 7

Dry ampoule containing 2.5 mg of active substance per 1 ml

| Composition: | |
|---|---|
| Active substance | 2.5 mg |
| Mannitol | 50.0 mg |
| Water for injections ad | 1.0 ml |

Preparation:

The active substance and mannitol are dissolved in water. After transferring the solution to the ampoule, it is freeze-dried.

At the point of use, the solution is made up with water for injections.

EXAMPLE 8

Tablet containing 50 mg of active substance

| Composition: | |
|---|---|
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

EXAMPLE 9

Tablet containing 350 mg of active substance

| Composition: | |
|---|---|
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

EXAMPLE 10

Capsules containing 50 mg of active substance

| Composition: | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This triturate is added to the mixture of (2) and (4), with thorough mixing.

This powdered mixture is packed into size 3 hard gelatin oblong capsules in a capsule filling machine.

EXAMPLE 11

Capsules containing 350 mg of active substance

| Composition: | |
|---|---|
| (1) Active substance | 350.0 mg |
| (2) Dried corn starch | 46.0 mg |
| (3) Powdered lactose | 30.0 mg |
| (4) Magnesium stearate | 4.0 mg |
| | 430.0 mg |

Preparation:

(1) is triturated with (3). This triturate is added to the mixture of (2) and (4), with thorough mixing.

This powdered mixture is packed into size 0 hard gelatin oblong capsules in a capsule filling machine.

What is claimed is:

1. (3S,5S)-5-[(4'-amidino-4-biphenylyl)oxymethyl]-3-[[[1-(cyclohexyloxycarbonyloxy)ethyl]oxycarbonyl]methyl]-2-pyrrolidinone or a pharmaceutically acceptable salt thereof.

2. A cyclic imino derivative, selected from the group consisting of:

(3S,5S)-5-[(4'-acetoxymethyloxycarbonylamidino-4-biphenylyl)oxymethyl]-3-[(methoxycarbonyl)methyl]-2-pyrrolidinone, (3S,5S)-5-[[4'-(1-acetoxyethyl)oxycarbonylamidino-4-biphenylyl]oxymethyl]-3-[(methoxycarbonyl)methyl]-2-pyrrolidinone, (3S,5S)-5-[(4'-benzyloxycarbonylamidino-4-biphenylyl)oxymethyl]-3-[[[1-(cyclohexyloxycarbonyloxy)ethyl]oxycarbonyl]-methyl]-2-pyrrolidinone, (3S,5S)-5-[(4'-benzyloxycarbonylamidino-4-biphenylyl)oxymethyl]-3-[[[1-(ethyloxycarbonyloxy)ethyl]oxycarbonyl]-methyl]-2-pyrrolidinone, (3S,5S)-5-[(4'-benzyloxycarbonylamidino-4-biphenylyl)oxymethyl]-3-[(pivaloyloxymethyloxycarbonyl)methyl]-2-pyrrolidinone, (3S,5S)-5-[(4'-methoxycarbonylamidino-4-biphenylyl)oxymethyl]-3-[(pivaloyloxymethyloxycarbonyl)methyl]-2-pyrrolidinone, (3S,5S)-5-[(4'-amidino-4-biphenylyl)oxymethyl]-3-[[[1-(cyclohexyloxycarbonyloxy)ethyl]oxycarbonyl]methyl]-2-pyrrolidinone, (3S,5S)-5-[(4'-amidino-4-biphenylyl)oxymethyl]-3-[[[1(ethyloxycarbonyloxy)ethyl]oxycarbonyl]methyl]-2-pyrrolidinone, (3S,5S)-5-[(4'-amidino-4-biphenylyl)oxymethyl]-3-[(pivaloyloxymethyloxycarbonyl)methyl]-2-pyrrolidinone, (3S,5S)-5-[(4'-amidino-4-biphenylyl)oxymethyl]-3-[(cyclohexyloxycarbonyl)methyl]-2-pyrrolidinone, (3S,5S)-5-[(4'-amidino-4-biphenylyl)oxymethyl]-3-[(cyclohexylmethyloxycarbonyl)methyl]-2-pyrrolidinone, (3S,5S)-5-[(4'-amidino-4-biphenylyl)oxymethyl]-3-[(cyclopentyloxycarbonyl)methyl]-2-pyrrolidinone, (3S,5S)-5-[(4'-amidino-4-biphenylyl)oxymethyl]-3-[(cycloheptyloxycarbonyl)methyl]-2-pyrrolidinone, (3S,5S)-3-[(cyclohexyloxycarbonyl)methyl]-5-[(4'methoxycarbonylamidino-4-biphenyl)oxymethyl]-2-pyrrolidinone, (3S,5S)-5-[[4'-(O,O'-diethylphosphono)amidino-4-biphenylyl]oxymethyl]-3-[(methoxycarbonyl)methyl]-2-pyrrolidinone, and pharmaceutically acceptable salts thereof.

3. A cyclic imino derivative of the formula

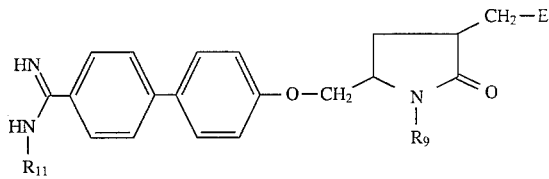

wherein (with the proviso that if $R_{11}$ represents H, methoxycarbonyl ethoxycarbonyl or benzyloxycarbonyl and E represents $R_8O-CO-$, then $R_8$ represents a $C_{5-7}$-cycloalkyl or $C_{5-7}$-cycloalkylmethyl group $R_9$ represents a hydrogen atom, $R_{11}$ represents a hydrogen atom, methoxycarbonyl, ethoxycarbonyl, benzyloxycarbonyl, an $R_1-CO-O-(R_2CR_3)-O-CO-$ or $(R_4O)PO(OR_5)-$ group, whereby $R_1$ represents a methyl group, $R_2$ represents a hydrogen atom or a methyl group, $R_3$ represents a hydrogen atom, $R_4$ and $R_5$, which may be identical or different, represent methyl or ethyl groups;

E represent an $R_6-CO-O-CHR_7-O-CO-$ or $R_8O-CO-$ group, wherein $R_6$ represents a tert-butyl, ethoxy or cyclohexyloxy group, $R_7$ represents a hydrogen atom or a methyl group, and $R_8$ represents a hydrogen atom, a methyl, ethyl, $C_{5-7}$-cycloalkyl or $C_{5-7}$-cycloalkylmethyl group or a tautomer or pharmaceutically acceptable salt thereof.

4. A pharmaceutical composition useful for the treatment of thrombosis, comprising a therapeutically effective amount of a cyclic imino derivative as recited in any one of claims 1, 2 or 3, and one or more inert carriers or diluents.

5. A method for treating thrombosis in a patient, which comprises administering to the patient a therapeutically effective amount of a cyclic imino derivative as recited in any one of claims 1, 2 or 3.

* * * * *